(12) United States Patent
Foster et al.

(10) Patent No.: US 10,853,455 B2
(45) Date of Patent: Dec. 1, 2020

(54) CARE MANAGEMENT OUTREACH

(71) Applicant: CERNER INNOVATION, INC., Kansas City, KS (US)

(72) Inventors: Allison D. Foster, Liberty, MO (US); Bharat B. Sutariya, Parkville, MO (US); Jaclynne L. Aagesen, Parkville, MO (US)

(*) Notice: Subject to any disclaimer, the term of this patent is extended or adjusted under 35 U.S.C. 154(b) by 830 days.

(21) Appl. No.: 14/586,249

(22) Filed: Dec. 30, 2014

(65) Prior Publication Data

US 2016/0125150 A1 May 5, 2016

Related U.S. Application Data

(60) Provisional application No. 62/073,254, filed on Oct. 31, 2014.

(51) Int. Cl.
*G16H 50/20* (2018.01)
*G06F 19/00* (2018.01)
*G16H 40/20* (2018.01)
*G16H 50/30* (2018.01)
*G16H 10/60* (2018.01)

(52) U.S. Cl.
CPC ......... *G06F 19/3481* (2013.01); *G16H 10/60* (2018.01); *G16H 40/20* (2018.01); *G16H 50/20* (2018.01); *G16H 50/30* (2018.01)

(58) Field of Classification Search
None
See application file for complete search history.

(56) References Cited

U.S. PATENT DOCUMENTS

| 6,283,761 | B1 | 9/2001 | Joao | |
|---|---|---|---|---|
| 2002/0123906 | A1* | 9/2002 | Goetzke | G16H 50/50 705/2 |
| 2003/0167184 | A1* | 9/2003 | Kole | G06Q 10/10 705/2 |
| 2005/0216313 | A1* | 9/2005 | Claud | G06Q 50/22 705/3 |
| 2006/0053035 | A1 | 3/2006 | Eisenberg | |
| 2007/0192132 | A1 | 8/2007 | Thesman | |

(Continued)

OTHER PUBLICATIONS

Final Office Action dated Mar. 26, 2018 in U.S. Appl. No. 14/586,126, 44 pages.

(Continued)

*Primary Examiner* — Michael Tomaszewski
(74) *Attorney, Agent, or Firm* — Shook, Hardy & Bacon, L.L.P.

(57) ABSTRACT

Methods, systems, and computer-readable media are provided for automatically generating outreach events for a care management service. Patient health data is received and processed to determine that a patient is eligible for care management services. Upon determining that the patient is eligible for care management services, a welcome-to-service template is selected, populated with patient-specific information, and communicated to the patient. The patient's health data is monitored to determine if there has been a change in care management status for the patient. Upon detecting a change in status, an appropriate template is selected, populated with patient-specific information, and communicated to the patient and/or a care team caring for the patient.

20 Claims, 13 Drawing Sheets

(56) References Cited

U.S. PATENT DOCUMENTS

| | | |
|---|---|---|
| 2009/0319296 A1 | 12/2009 | Schoenberg |
| 2010/0250279 A1* | 9/2010 | Guggenheim ......... G06Q 50/22 |
| | | 705/3 |
| 2013/0030825 A1 | 1/2013 | Bagwandeen et al. |
| 2013/0096943 A1* | 4/2013 | Carey ................. G06F 21/6263 |
| | | 705/2 |
| 2013/0290007 A1* | 10/2013 | Haq ....................... G06Q 50/22 |
| | | 705/2 |
| 2014/0164017 A1 | 6/2014 | Merkin |
| 2014/0181128 A1 | 6/2014 | Riskin et al. |
| 2015/0088540 A1* | 3/2015 | Lo .......................... G06F 19/328 |
| | | 705/2 |
| 2015/0095056 A1 | 4/2015 | Ryan et al. |
| 2016/0098520 A1 | 4/2016 | Lulias et al. |
| 2016/0125150 A1* | 5/2016 | Foster ..................... G16H 10/60 |
| | | 705/3 |
| 2016/0125168 A1* | 5/2016 | Aagesen ............. G06F 19/3481 |
| | | 705/3 |

OTHER PUBLICATIONS

Final Office Action dated Apr. 6, 2018 in U.S. Appl. No. 14/584,644, 23 pages.
Non-Final Office Action received for U.S. Appl. No. 14/586,126, dated Nov. 7, 2018, 51 pages.
First Action Interview Pre-Interview Communication dated Jun. 5, 2017 in U.S. Appl. No. 14/584,644, 5 pages.
First Action Interview Pre-Interview Communication dated Aug. 24, 2017 in U.S. Appl. No. 14/586,126, 8 pages.
Non-Final Office Action dated Sep. 19, 2017 in U.S. Appl. No. 14/584,644, 20 pages.
First Action Interview Office Action dated Oct. 13, 2017 in U.S. Appl. No. 14/586,126, 10 pages.
Non-Final Office Action received for U.S. Appl. No. 14/586,126, dated Jun. 18, 2020, 49 pages.

* cited by examiner

CARE MANAGEMENT OUTREACH

CROSS-REFERENCE TO RELATED APPLICATIONS

This application entitled "Care Management Outreach," claims priority to U.S. Provisional Application 62/073,254, filed Oct. 31, 2014. The entirety of the aforementioned application is incorporated by reference herein.

This application entitled "Care Management Outreach" is related by subject matter to concurrently filed U.S. patent application Ser. No. 14/584,644, entitled "Identification, Stratification, and Prioritization of Patients Who Qualify for Care Management Services;" and U.S. patent application Ser. No. 14/586,126, and entitled "Care Manager Assignment and Alignment." The entireties of the aforementioned applications are incorporated by reference herein.

BACKGROUND

Care management refers to activities that are intended to improve a patient's health status, coordinate the patient's care across different care venues, reduce the patient's need for medical services, and ultimately decrease the amount of money spent on healthcare services for the patient. Effective care management relies on care managers to engage with patients and affect the care management goals. Care managers are generally licensed personnel (R.N., L.P.N., and/or licensed social workers) who may be affiliated with a provider or a provider's office, an insurance company, or a hospital.

Care managers face a number of challenges when attempting to implement effective care management practices. One of these challenges is the fragmentation of patient care over multiple clinical care venues. For instance, a patient may utilize an ambulatory care clinic, an emergency department, a post-acute care facility, and home health services in the course of the patient's care over, for example, a period of one year. These disparate facilities often do not share the patient's clinical information with each other, and so a care manager affiliated with, for example, the ambulatory care clinic may only have access to the patient's health data from that particular clinic. The care manager's ability to provide effective care management is limited by being able to access only a limited portion of the patient's health profile.

Another problem faced by care managers is the inability to view the patient's health history over the span of the patient's life. This type of health record, known as a longitudinal patient record often does not exist due to the difficulties in compiling the data needed to generate the record. Although it may be possible to cobble together a semblance of a longitudinal medical record by interviewing the patient, this approach generally leaves major gaps and/or inaccuracies in the record. Instead of being able to access the patient's longitudinal medical record, care managers often only have access to a patient's health data compiled at a particular care venue. This health data is limited to the time period in which the patient has utilized the particular venue, and in today's mobile world, this time period may only account for a small fraction of the patient's total medical history. The care manager's efforts to provide effective care management are further stymied by being provided with only a small glimpse of a patient's total health profile.

Although traditional enterprise care management solutions have tried to address some of the shortcomings noted above, they have generally fallen short as they rely almost exclusively on insurance claims data when determining if the patient is eligible for care management services. Utilizing only insurance claims data has several shortcomings. For example, insurance claims data is often compiled weeks to months after a patient event has occurred such as a visit to an emergency department, a readmission to a hospital, and the like. Because claims data is retroactive in nature, care managers are unable to timely identify patients who may need care management services. As an example, a patient may have died or the patient's insurance eligibility for care management services may have expired in the lag period between when a patient event occurred and when information from the insurance claim is available to a care manager. Moreover, insurance claims data provides only a limited profile of the patient—a profile that fails to take into account such things as the patient's longitudinal medical record, the patient's socioeconomic status, the patient's support system, the patient's preferences regarding his/her care, and the like. These factors may make or break the difference between effective care management and ineffective care management.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, an enterprise care management solution for automatically and without human intervention generating outreach events for a care management service. The enterprise care management solution may be implemented as a system, a computerized method, and as computer-readable media. Health data for a patient is compiled and processed at a central location. The health data includes patient electronic medical record data received from a plurality of disparate care venues as well as insurance claims data. The health data is processed to determine whether the patient is eligible for care management services. For instance, patients may be determined to be eligible for care management services when they meet certain criteria directed to, for instance, disease burden, amount of healthcare system utilization, and amount of healthcare spend. The health data may also be processed to determine if the patient is eligible for one or more health intervention programs such as, for example, a diabetes management program, a hypertension management program, an obesity management program, and the like.

Continuing, once it is determined that the patient is eligible for care management services and, optionally, one or more health intervention programs, a welcome-to-service template is automatically populated with patient-specific information and is communicated to the patient. In the case where the patient is identified as being eligible for one or more health intervention programs, the welcome-to-service letter may also be automatically populated with information about the health intervention program including any patient-specific recommendations associated with the program.

The enterprise care management solution is further configured to monitor the patient's health data to determine whether there is a change in care management status for the patient. Exemplary changes in status may comprise the patient agreeing to enroll in the care management service, the patient declining to enroll in the care management service, the patient no longer being eligible for care management services, and/or the care management services being suspended for the patient. Upon detecting a change in status, a template that is customized for the particular change in status is automatically populated with patient-specific information and is automatically communicated to the patient.

The enterprise care management solution described herein is additionally configured to determine when a care manager updates a patient's care plan. Upon detecting an update, an option may be presented to the care manager enabling the care manager to automatically populate a template with information pertaining to the update. The populated template may then be automatically communicated to the patient and/or the patient's care team.

BRIEF DESCRIPTION OF THE DRAWINGS

Embodiments are described in detail below with reference to the attached drawing figures, wherein.

DETAILED DESCRIPTION

Figure 1:
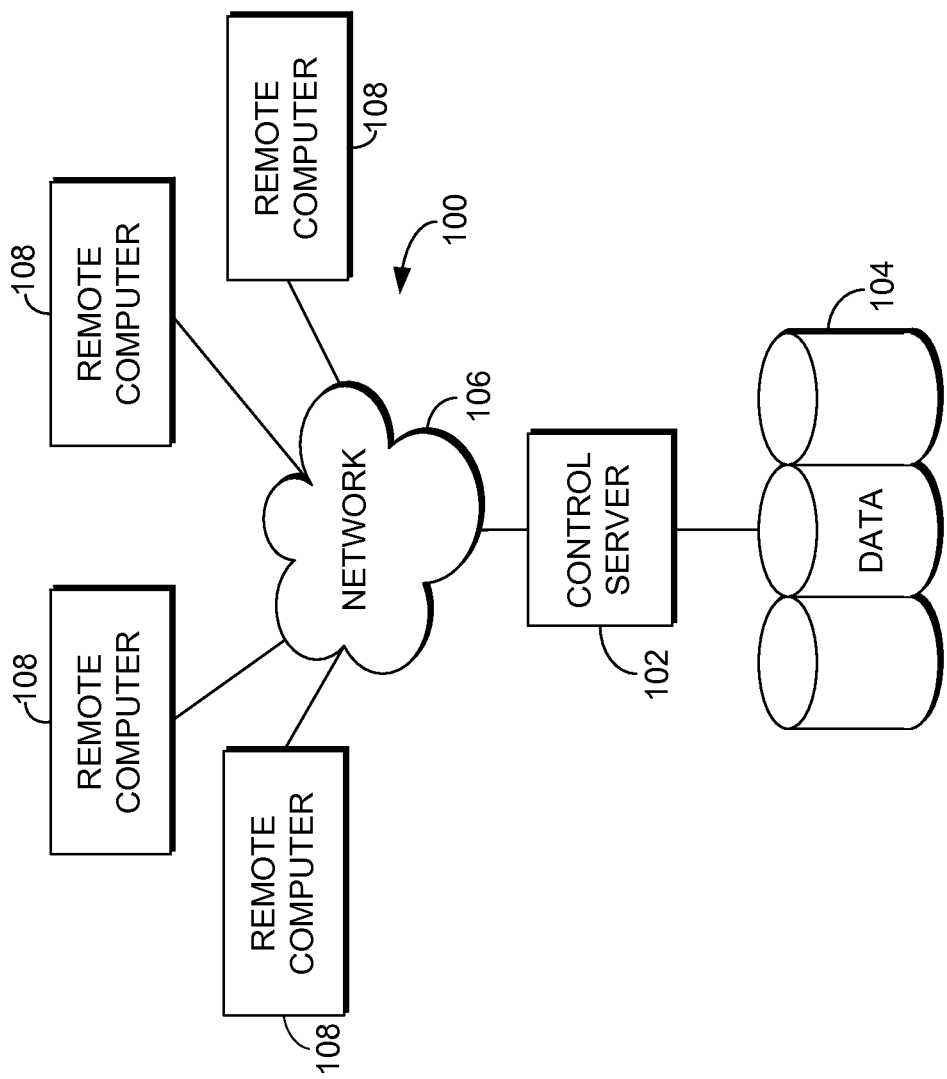
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Aspects described herein are directed to an enterprise care management system that identifies, stratifies, and prioritizes patients who are eligible for care management services, aligns the identified patients with appropriate care managers, and automatically generates outreach events related to care management. As explained more fully below, the care management system is implemented as a cloud computing platform that continuously receives and processes health data collected from a plurality of disparate data sources. The health data may comprise, for example, electronic medical record data for a population of patients, community-derived data, as well as insurance claims data. As mentioned, the data is received from a plurality of disparate sources such as ambulatory care clinics, insurance providers, physician offices, hospitals, home health services, long-term care facilities, rehabilitation facilities, county health clinics, public health agencies, and the like. These sources are disparate in that they may bear no financial, business, and/or legal relationship to each other, and they do not share patient health data with each other. The amount of data generated from these sources is often immense. For instance, the care management system may receive health data for up to 2,000,000 patients.

Once received, the health data is leveraged in a number of different ways. For example, for a particular patient, the patient's health data may be used to determine whether the patient is eligible for care management services. In this instance, the health data for the patient may be aggregated from the different sources and processed to determine a disease burden associated with the patient, an amount of health system utilization by the patient, and/or the amount of money spent on healthcare for the patient. When the patient exceeds a predetermined threshold value associated with one or more of the criteria, the patient is identified as being eligible for care management services. Once identified, the patient may be stratified into a category such as high-risk senior, high-risk adult, high-risk pediatrics, or high-risk maternity and a priority level may be assigned to the patient based on, for instance, one or more risk models.

After identification, stratification, and prioritization, the health data may further be used to generated a patient profile for the patient that includes such things as the clinical characteristics of the patient, providers currently caring for the patient, geographic location of the patient, the patient's socioeconomic status, literacy status, and ambulation status, the patient's support system, patient preferences regarding, for example, language or preferred gender of provider, and the amount of clinical contact needed by the patient. The care management system is also able to access data stores containing information about care managers. The information may comprise clinical expertise of the care manager, geographic location of the care manager, a provider or healthcare facility with whom the care manager is affiliated, geographical location of the care manager, workload capacity of the care manager, and/or previous care management outcome data associated with the care manager. Using these two sets of information (e.g., the patient profile and the information concerning the care managers), the system aligns the patient with a care manager who is most suited to help the patient meet his/her care management goals.

Once a patient identified as being eligible for care management services has been aligned with a care manager, the patient's health data is further used by the care management system to automatically generate outreach events for the patient related to the care management services. For example, a welcome-to-service template may be automatically populated with patient-specific information and communicated to the patient and, optionally, the patient's care team. The care management system continually monitors the patient's health data to determine if a care management status change has occurred such as the patient registering for care management services, the patient declining care management services, the patient no longer being eligible for care management services, or care management services being suspended for the patient. Once a status change is detected, a template customized to the particular status change is populated with patient-specific information and is communicated to the patient and/or the patient's care team. Additionally, the care management system is configured to detect when an update has been made to a particular patient's care plan. Upon detecting an update, the care manager is presented with an option to populate a template with information concerning the update. The populated template is then automatically communicated to the patient and/or the patient's care team.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise non-transitory computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
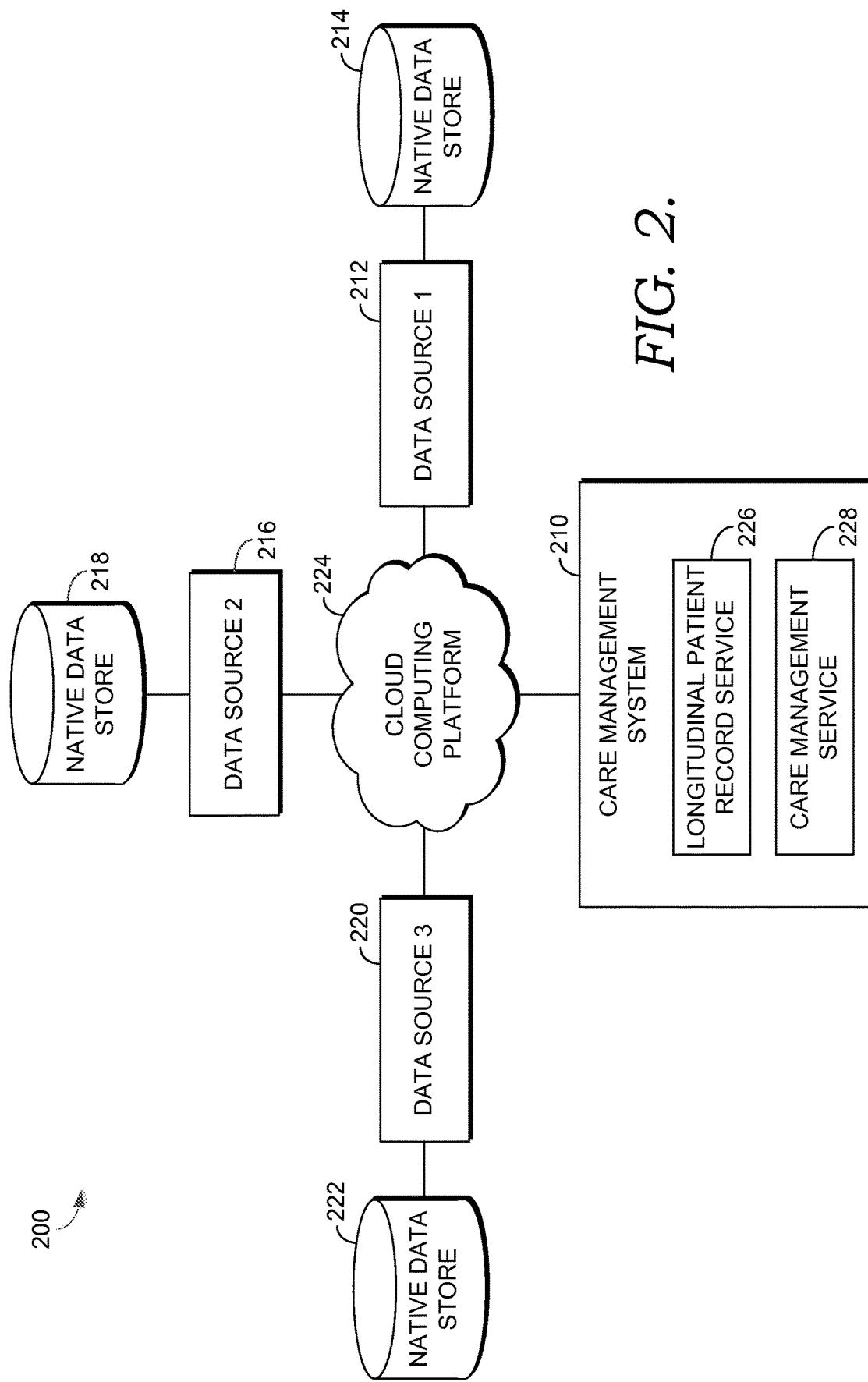
FIG. 2 is a block diagram showing an exemplary architecture for facilitating the collection and processing of patient population health data by a care management system suitable to implement embodiments of the present invention.

Turning now to FIG. 2, a block diagram 200 is illustrated, in accordance with an embodiment of the present invention, showing an exemplary cloud computing platform 224 for use by a care management system 210. It will be understood and appreciated that the cloud computing platform 224 shown in FIG. 2 is merely an example of one suitable computing system environment and is not intended to suggest any limitation as to the scope of use or functionality of embodiments of the present invention. For instance, the cloud computing platform 224 may be a public cloud, a private cloud, or a dedicated cloud. Neither should the cloud computing platform 224 be interpreted as having any dependency or requirement related to any single component or combination of components illustrated therein. Further, although the various blocks of FIG. 2 are shown with lines for the sake of clarity, in reality, delineating various components is not so clear, and metaphorically, the lines would more accurately be grey and fuzzy. In addition, any number of physical machines, virtual machines, data centers, endpoints, or combinations thereof may be employed to achieve the desired functionality within the scope of embodiments of the present invention. As mentioned, the cloud computing platform 224 comprises a cloud-computing network or an enterprise computing network, which is known in the art as "the cloud."

The cloud computing platform 224 includes a data center configured to host and support the operation of the system 210. The system 210 refers to any software, or portions of software, that runs on top of, or accesses storage locations within, the platform 224. It will be appreciated that cloud computing platform 224 may include multiple computing devices such as computing devices or portions of computing devices 100 shown in FIG. 1. Cloud computing platform 224 may include virtual machines, such as software, applications, operating systems, or programs that are executed by a processing unit to underlie the functionality of the care management system 210. Further, the virtual machines may include processing capacity, storage locations, and other assets to support the care management system 210.

In one aspect, the cloud computing platform 224 can communicate internally through connections dynamically made between the virtual machines and computing devices and externally through a physical network topology to resources of a remote network such as with data sources 212, 216, and 220. By way of example, the connections may include, without limitation, one or more local area networks (LANs) and/or wide area networks (WANs). Such networking environments are commonplace in offices, enterprise-wide computer networks, intranets, and the Internet. Accordingly, the network is not further described herein.

As shown in FIG. 2, the care management system 210 is capable of communicating with a number of different data sources, such as the data sources 212, 216, and 220 for the collection of patient population health data. As used throughout this application, the term "patient population health data" or "patient health data" is meant to be broad and encompass many types of healthcare information found in a healthcare environment. For example, patient population health data may include information that describes various aspects of the patient state, including patient vitals, lab results, medication orders, diagnosis codes, condition codes, clinical orders, indexed values from clinical notes or other text documents, patient demographic information, patient history, patient images, and a variety of other patient information. It may also include information concerning for example, the patient's ambulation status, socioeconomic status, literacy status, and the like.

The data sources 212, 216, and 220 may include, for example, hospitals, physician offices, health information exchanges, insurance providers, nursing homes, pharmacies, home health services, urgent care clinics, continuity of care documents (CCDs), and the like. In exemplary aspects, the data sources 212, 216, and 220 may be responsible for managing the health of a population of patients. As part of this management, the data sources 212, 216, and 220 may implement care management programs designed to improve patient health status, coordinate patient care across different care venues, reduce patient need for medical services, and ultimately decrease the amount of money spent on healthcare services for the patient population. The care management system 210 enables these data sources 212, 216, and 220 to not only identify patients within the patient population most in need of care management services, but provide tools for aligning the identified patients with effective care managers, and generating appropriate outreach events for these patients.

It should be noted that the data sources shown as communicating with the care management system 210 in FIG. 2 are provided by way of example only and are not intended to limit the scope of the present invention in any way. Each data source 212, 216, and 220 may have one or more computing devices such as computing device 100 of FIG. 1, for communicating with the care management system 210. Each data source 212, 216, and 220 may maintain its own native electronic medical record system represented by a native data store 214, a native data store 218, and a native data store 222 associated with the first, second, and third data sources 212, 216, and 220 respectively. Further, the data sources 212, 216, and 220 may not be directly or indirectly connected with one another such that the native data stores 214, 218, and 222 are utilized only by the data stores' respective healthcare facility. The data sources 212, 216, and 220 send information to the cloud computing platform 224 and not typically directly between one another. In other words, the data sources 212, 216, and 220 generally do not share patient electronic medical record data with each other. In addition, communication between the system 210 and the various data sources 212, 216, and 220 may be via one or more networks, which may comprise one or more wide area networks (WANs) and one or more local area networks (LANs), as well as one or more public networks, such as the Internet, and one or more private networks.

The care management system 210 comprises a longitudinal patient record service 226 and a care management service 228. Aspects associated with the longitudinal patient record service 226 will be explained in greater depth with respect to FIG. 3, and aspects of the care management service 228 will be explained in greater depth with respect to FIG. 4.

Figure 3:
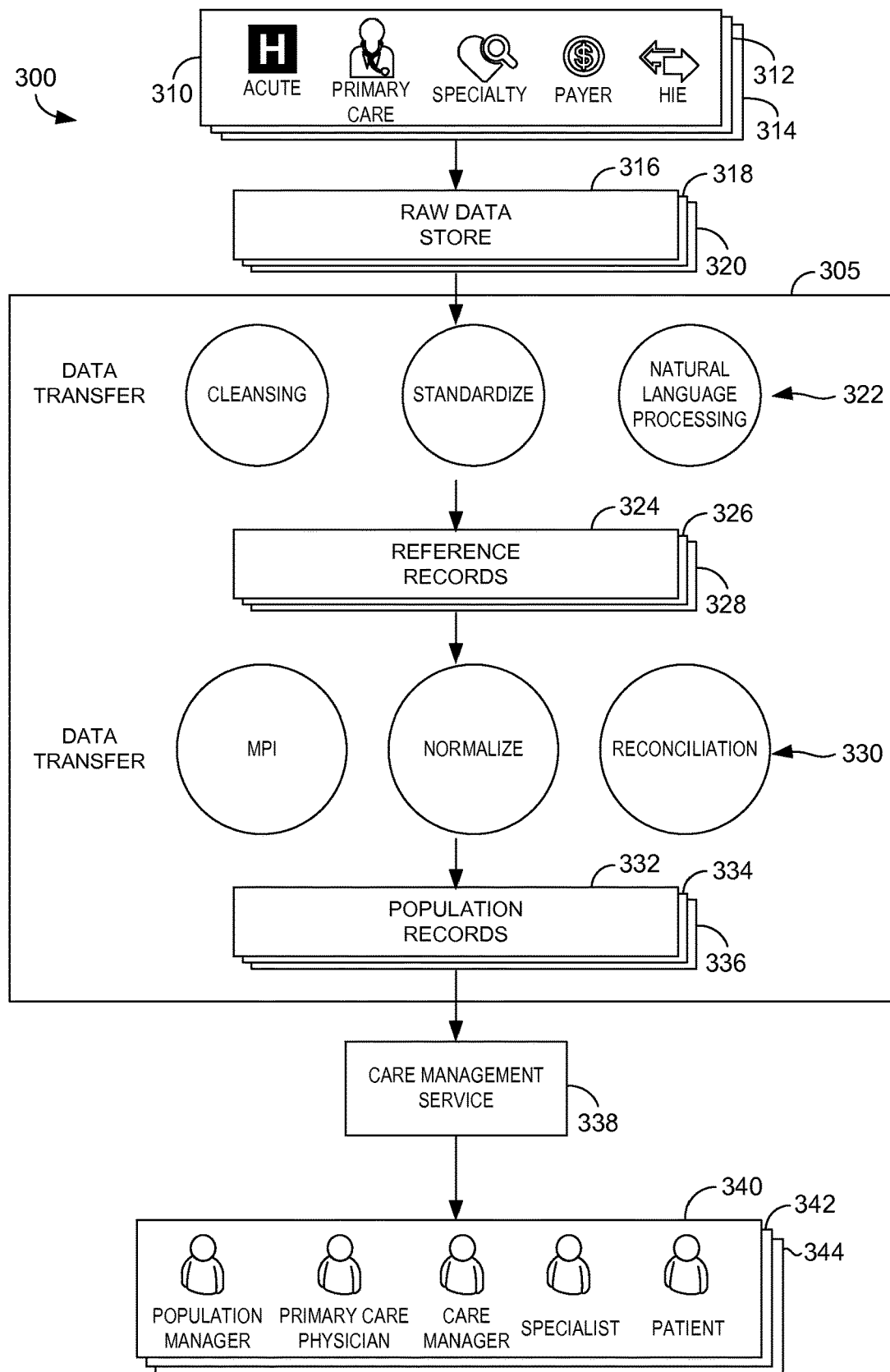
FIG. 3 is a schematic illustration of processing steps carried out by a care management system in accordance with an embodiment of the present invention.

FIG. 3 is a schematic illustration depicting relationships between data sources, such as the data sources 212, 216, and 220 of FIG. 2, and processes carried out by the longitudinal patient record service 226 of FIG. 2, now labelled as longitudinal patient record service 305. Raw data sources 310, 312, and 314 include such sources as acute care facilities, primary care providers, specialty providers, payers, HIEs, pharmacies, patient-inputted information, public health agencies, community sources, and the like. Additional data sources beyond those shown are contemplated. The raw data sources 310, 312, 314 may contribute data in a variety of nomenclatures and formats, including proprietary formats. The raw data received from the raw data sources 310, 312, and 314 is stored by source in raw data stores 316, 318, and 320. The raw data stores 316, 318, and 320 may be networked storage or distributed storage including storage on servers located in the cloud.

At a step 322, the longitudinal patient record service 305 transforms the raw data into industry-standard nomenclatures by, for example, utilizing techniques such as cleaning, standardizing, natural language processing, machine learning, and the like. After transformation at step 322, the transformed data is stored in reference records 324, 326, and 328. Each reference record 324, 326, and 328 stores transformed data from a single data source. The reference records 324, 326, and 328 may be networked storage or distributed storage including storage on servers located in the cloud.

At a step 330, the longitudinal patient record service 305 combines data from the reference records 324, 326, and 328 and transforms the data a second time before storing the data in longitudinal patient records 332, 334, and 336 for each patient in the population. Each record is longitudinal in that it contains information on all of the patient's health encounters even though the encounters may have occurred at disparate locations, with disparate providers, and at different times. The longitudinal patient records 332, 334, and 336 may be networked storage or distributed storage including storage on servers located in the cloud.

The longitudinal patient record service 305 utilizes one or more probabilistic patient matching algorithms to match patients with their data and create the person-centric longitudinal patient records at the step 330. The probabilistic patient matching algorithms may match patients to their clinical, financial, and activity data. Patients may be matched to their data based on for example, patient name, patient identifiers, and the like. For more general data such as, for example, socioeconomic condition data, a patient may be matched to an appropriate set of socioeconomic data using, for example, the patient's zip code. The longitudinal patient record service 305 is also configured to reconcile all of the patient's records even if the records are associated with different patient identifiers. For instance, a pharmacy may use a first patient identifier when dispensing medications to a patient while a care clinic may use a second patient identifier when treating the patient. The longitudinal patient record service 305 is configured to reconcile these patient identifiers and match all of the pertinent medical information associated with the patient. Each patient's data is also normalized via grouping codes from multiple terminologies that mean the same thing thereby reducing redundant data.

Different programs, such as the care management service 228, now labelled as care management service 338, are able to access the longitudinal patient records 332, 334, and 336. Further, different end users are able to utilize the output of the care manager service 338 via one or more computer applications 340, 342, and 344. End-users are numerous but representative examples include care managers, primary care physicians, specialists, patients, healthcare organization administrators, healthcare facilities, payers, and the like. The computer applications 340, 342, and 344 may comprise, for example, applications that identify, stratify, and prioritize patients eligible for care management services, applications that align patients eligible for care management services with appropriate care managers, and applications that generate outreach events related to care management.

Figure 4:
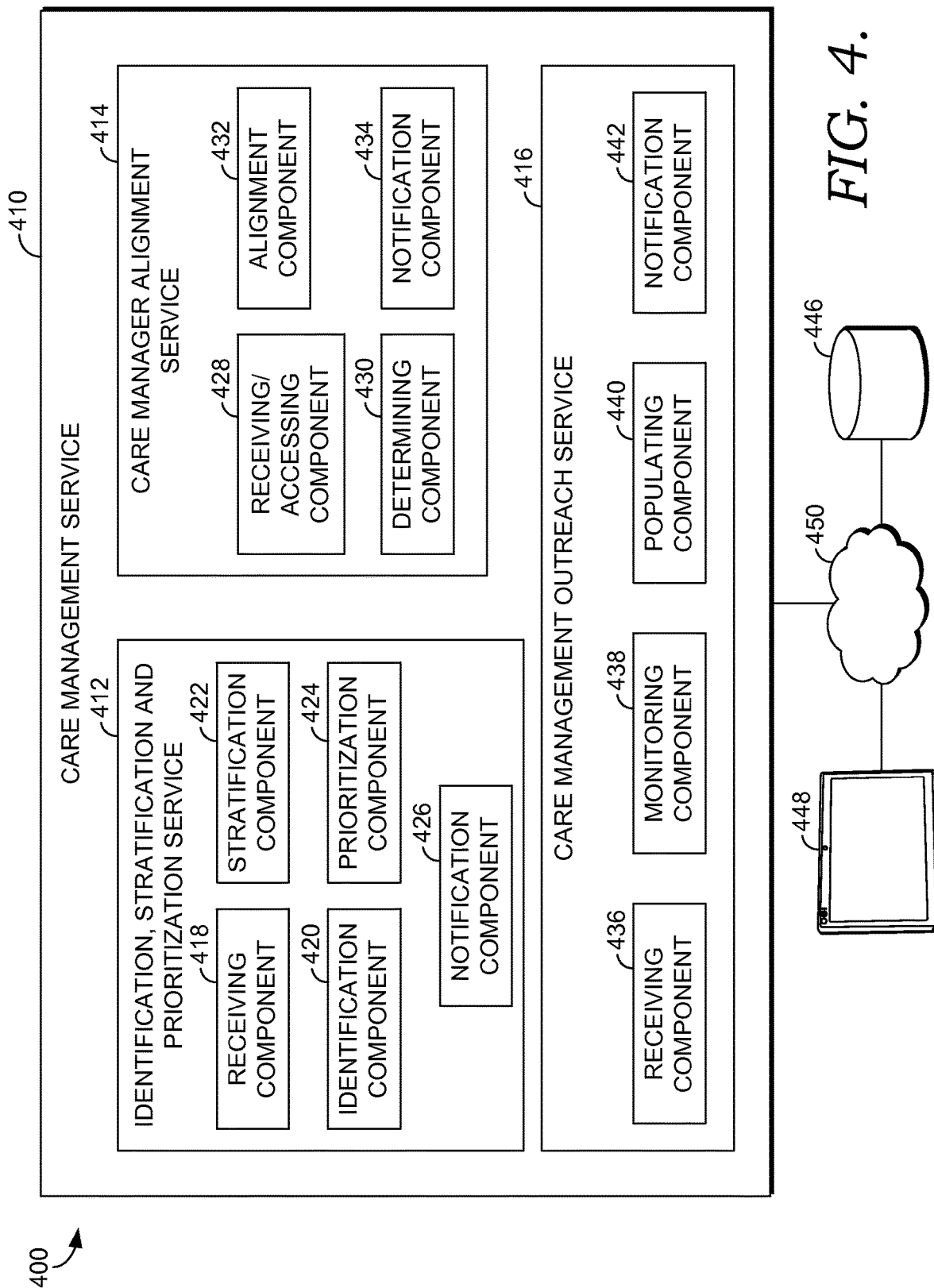
FIG. 4 is a block diagram of an exemplary care management service suitable to implement embodiments of the present invention.

Turning now to FIG. 4, the care management service 228 of the care management system 210, now labeled as care management service 410, is depicted suitable for use in implementing embodiments of the present invention. The care management service 410 is merely an example of one suitable computing system environment and is not intended to suggest any limitation as to the scope of use or functionality of embodiments of the present invention. Neither should the care management service 410 be interpreted as having any dependency or requirement related to any single module/component or combination of modules/components illustrated therein.

The care management service 410 includes a number of services such as an identification, stratification, and prioritization service 412, a care manager alignment service 414, and a care management outreach service 416. Each of the services 412, 414, and 416 may be in communication with one another via a network 450. The network 450 may include, without limitation, one or more local area networks (LANs) or wide area networks (WANs). The network 450 may be a secure network associated with a healthcare facility. The secure network 450 may require that a user log in and be authenticated in order to send and/or receive information over the network 450. Additionally, each of the services 412, 414, and 416 are in communication with a data store 446 and an end-user computing device 448 having a display screen.

Although the services 412, 414, and 416 are depicted as separate services, it is contemplated that the services may be combined into one service. Additionally, although each service 412, 414, and 416 is depicted as having its own components, in reality a component, such as a notification component may be shared by the different services 412, 414, and 416. The services 412, 414, and 416 are depicted separately to facilitate ease of explanation for each of the services 412, 414, and 416.

In some embodiments, one or more of the illustrated components/modules may be implemented as stand-along applications. In other embodiments, one or more of the illustrated components/modules may be integrated directly into the operating system of the services 412, 414, and 416. The components/modules illustrated in FIG. 4 are exemplary in nature and in number and should not be construed as limiting. Any number of components/modules may be employed to achieve the desired functionality within the scope of embodiments hereof. Further, the services 412, 414, and 416 may be located on any number of servers. By way of example only, the identification, stratification, and prioritization service 412 might reside on a server, a cluster of servers, or a computing device remote from one or more of the remaining services.

The depiction of the care management service 410 is merely exemplary. While the services 412, 414, and 416 are illustrated as single units, it will be appreciated that the services 412, 414, and 416 are scalable. For example, each service may in actuality include a plurality of computing devices in communication with one another. Moreover, the data store 446, or portions thereof, may be included within, for instance, the services 412, 414, and 416 as a computer-storage medium. The single unit depictions are meant for clarity, not to limit the scope of embodiments in any form.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The data store 446 is configured to store information for use by, for example, the services 412, 414, and 416 and the end-user computing device 448. The information stored in association with the data store 446 is configured to be searchable for one or more items of information stored in association therewith. The information stored in association with the data store 446 may comprise general information used by the services 412, 414, and 416 and/or the end-user computing device 448.

In one aspect, the data store 446 stores electronic medical record data for a plurality of patients. In aspects, the electronic medical record data may be in the form of longitudinal patient records. As described above, longitudinal patient record data may comprise electronic clinical documents such as images, clinical notes, orders, summaries, reports, analyses, or other types of electronic medical documentation relevant to a particular patient's condition and/or treatment over the lifetime of the patient. Electronic clinical documents contain various types of information relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

Additionally, the data store 446 may store insurance claims data for a plurality of patients. As well, the data store 446 stores information concerning decision-support algorithms, differential or possible diagnoses algorithms, reference materials, standards of care, recommendation protocols, risk models, alert protocols, and the like. This information may be promulgated by, for example, third-party content providers, healthcare facilities, nationally-recognized medical organizations, and the like. The data store 446 may also store information concerning staffing assignments and/or clinicians and care teams assigned to care for a patient. Additionally, the data store 446 may store information regarding characteristics of care managers such as, for example, clinical expertise of the care manager, quality outcomes associated with care managers, who a care manager is associated with (e.g., a particular provider, an insurance company, a hospital, and the like), where the care manager is located geographically, and information on the workload capacity of the care manager.

The content and volume of such information in the data store 446 are not intended to limit the scope of embodiments of the present invention in any way. Further, though illustrated as a single, independent component, the data store 446 may, in fact, be a plurality of storage devices comprising networked storage or distributed storage including storage on servers located in the cloud.

As shown, the end-user computing device 448 includes the display screen that is configured to display information to the user of the end-user computing device 448, for instance, information relevant to communications initiated by and/or received by the end-user computing device 448, information concerning the identification of patients eligible for care management services, information relating to patient alignment with appropriate care managers, and information concerning outreach events related to care management. Embodiments are not intended to be limited to visual display but rather may also include audio presentation, combined audio/visual presentation, and the like. The end-user computing device 448 may be any type of display device suitable for presenting a graphical user interface. Such computing devices may include, without limitation, a computer, such as, for example, any of the remote computers 108 described above with reference to FIG. 1. Other types of display devices may include tablet PCs, PDAs, mobile phones, smart phones, as well as conventional display devices such as televisions. Interaction with the display screen of the end-user computing device 448 may be through conventional methods such as a mouse or a touch pad; interaction with the display screen may also occur through the use of gestures such as tapping, swiping, flicking, pinching, and the like.

Identification and Stratification of Patients Eligible for Care Management

The identification, stratification, and prioritization service 412 is configured to process data associated with a population of patients and identify those patients who are eligible for care management services. Further, these patients are stratified into different categories such as high-risk senior, high-risk adult, high-risk pediatrics, or high-risk maternity. Once categorized, the patients may be prioritized based on, for instance, a determined risk level. More particularly, the identification, stratification, and prioritization service 412 is configured to identify patients who suffer from multiple chronic conditions, have a high utilization of healthcare services including emergency department visits, and require a large number of medications to manage their conditions. It has been estimated that these patients, who generally account for only 5% of the patient population are responsible for the majority of dollars spent on healthcare. Therefore, it is important to identify these patients at an early point in the care process and encourage their enrollment in care management services.

As shown in FIG. 4, the identification, stratification, and prioritization service 412 comprises a receiving component 418, an identification component 420, a stratification component 422, a prioritization component 424, and a notification component 426. In some embodiments, one or more of the components 418, 420, 422, 424, and 426 may be implemented as stand-alone applications. In other embodiments, one or more of the components 418, 420, 422, 424, and 426 may be integrated directly into the operating system of a computing device such as the remote computer 108 of FIG. 1. It will be understood that the components 418, 420, 422, 424, and 426 illustrated in FIG. 4 are exemplary in nature and in number and should not be construed as limiting. Any number of components may be employed to achieve the desired functionality within the scope of embodiments hereof.

The receiving component 418 is configured for a variety of things. For instance, the receiving component 418 is configured to receive and/or access patient health data. As described above, the patient health data may comprise, for example, insurance claims data, longitudinal patient records compiled by the longitudinal patient record service 305 of FIG. 3, and other types of patient data. The patient data may be received from a variety of disparate data sources and be stored in association with, for instance, the data store 446.

The receiving component 418 is further configured to receive selections from one or more clients or end-users who utilize the identification, stratification, and prioritization service 412. Exemplary clients may comprise individual physicians, insurance companies, provider groups, hospitals, nursing homes, and the like. The client may customize how they wish to identify, stratify and prioritize patients eligible for care management services. For example, the clients may specify which criteria (i.e., disease burden, health system utilization, and/or healthcare spend) they want to utilize when identifying patients eligible for care management services, and they may further specify threshold parameters associated with each of the selected criteria. The clients may also specify the order in which the identification and stratification of patients is carried out by the identification, stratification, and prioritization service 412. As an example, the client may specify that its patient population first by stratified into categories such as senior, adult, pediatrics, and maternity, and that the identification criteria then be executed against each of these different categories to determine who is eligible for care management services. In another example, the client may specify that the identification process be carried out first, and the identified patients next be stratified into the different categories. Any and all such aspects, and any variation thereof, are contemplated as being within the scope discussed herein.

The identification component 420 is configured to identify patients who are eligible for care management services. To accomplish this, for each patient in the population the identification component 420 looks at one or more criteria comprising disease burden, amount of health system utilization, and amount of money spent on healthcare services. With respect to disease burden, the identification component 420 utilizes the patient's health data to determine whether the patient suffers from one or more disease conditions. The number of disease conditions encompasses any documented disease condition ranging from, for example, asthma to cancer. The disease conditions may comprise disease conditions typically associated with a pediatric population (e.g., juvenile rheumatoid arthritis, Type I diabetes mellitus) to disease conditions commonly associated with adults (e.g., hypertension, obesity, Type II diabetes mellitus), to disease conditions commonly associated with senior citizens (e.g., Parkinson's disease, Alzheimer's disease) to disease conditions associated with pregnancy (e.g., gestational diabetes, pre-eclampsia).

Continuing with respect to disease burden, the identification component 420 is further configured to use the patient health data to determine whether the patient has one or more disease conditions which have documented interactions with each other. For example, certain governing bodies such as the Centers for Medicare and Medicaid Services (CMS) have identified certain disease conditions that may interact with each other to cause a worsening of a patient's health. The identification component 420 may use this information (stored in association with, for instance, the data store 446) to determine whether the patient is suffering from these disease interactions. As well, the identification component 420 is configured to use the patient health data to determine whether the patient suffers from conditions typically associated with frailty such as, for example, malnutrition, incontinence, dementia, impaired vision, decubitus ulcers, weight loss, morbid obesity, history of falls, illiteracy, difficulty with ambulation, lack of a social support system, and the like.

The identification component 420 is also configured to determine an amount of health system utilization associated with each patient in the population. This can include both over-utilization of health system services, and under-utilization of health system services. Under-utilization may be problematic when, for example, the patient is pregnant but health data, including insurance claims data, indicates that the patient has not been seeking appropriate pre-natal care. Looking at patient health data, including insurance claims data, the identification component 420 determines the number of emergency department visits during a predefined period of time such as, for example, a rolling one year period, the number of inpatient admissions, the number of re-admissions to healthcare facilities for the same problem as the initial admission, the number of medications utilized by the patient, the amount and type of durable medical equipment (e.g., home oxygen use, use of a hospital bed in the patient's home, and the like) used by the patient, the number of provider visits during the predefined period of time, the number of laboratory and/or imaging procedures incurred by the patient during the predefined period of time, and the like.

The identification component 420 is also configured to determine the amount of dollars spent on healthcare services for the patient during the predefined period of time. This information may be derived from, for example, information from billing systems associated with the disparate data sources as well as insurance claims data. Further, the identification component 420 may analyze the pattern and frequency of current healthcare spend and compute a trajectory of a projected healthcare spend over a predefined period of time, such as a rolling one year period.

In aspects, the identification component 420 may apply one, two, or all three of the criteria to the health data. As described above, a client may configure which of the criteria the client wants to utilize when identifying patients eligible for care management services. For instance, a client may specify that just disease burden be utilized to determine eligible patients, or just health system utilization, or just amount of healthcare spend. In another example, the client may specify two of the criteria, and in yet another example, the client may specify that all three of the criteria be used to identify patients eligible for care management services. This feature enables the client to tailor the identification criteria to the client's specific situation. For example, the client may be a rural hospital that typically encounters a limited number of disease conditions but because of financial constraints wants to limit the amount of money spent on healthcare services. In this case, the client may specify amount of health system utilization and amount of healthcare spend as the criteria used to identify eligible patients. But a well-funded urban hospital that encounters a wide variety of disease conditions may specify disease burden as the sole criteria used to identify eligible patients. In an alternative aspect, the criteria used to identify eligible patients may be predefined.

The identification component 420 is also configured to apply a threshold parameter to each of the criteria. The threshold parameter may be configured by a client, such as a healthcare facility, or it may be predefined. As an example, a threshold parameter for disease burden may be that the patient must have five or more chronic conditions to qualify for care management services, and a threshold parameter for amount of health system utilization may be that the patient must have had ten emergency department visits within one year to qualify for care management services.

The stratification component 422 is configured to stratify the patient population into a category. As described above, the stratification component 422 may be instantiated before, after, or simultaneously with the identification component 420. When instantiated before the identification component 420, the stratification component 422 is configured use the health data, such as demographic data, to categorize the patient population into one of four categories: 1) senior; 2) adult; 3) pediatric; or 4) maternity. Seniors comprise patients 65 years of age or older, adults comprise patients between 18 and 64 years of age, pediatric patients comprise patients between 0 and 17 years of age, and maternity patients comprise patients who are pregnant. When instantiated after the identification component 420 has identified patients who are eligible for care management services, the stratification component 422 is configured to use health data, such as demographic data, to categorize the identified patients into one of four categories: 1) high-risk senior; 2) high-risk adult; 3) high-risk pediatrics; or 4) high-risk maternity.

Categorization of the patients into one of the four categories is useful when determining, for example, a care manager best suited to implement care management services for the patient, and/or when determining appropriate care recommendations for the patient. As an illustrative example, a patient classified as high-risk pediatric would be aligned with a care manager having expertise in pediatrics, while a patient classified as high-risk senior would be aligned with a care manager having geriatric expertise. And appropriate care recommendations would differ based on whether the patient is classified as, for instance, high-risk maternity as opposed to high-risk senior.

The prioritization component 424 is configured to use the patient health data to prioritize patients who have been determined to be eligible for care management services and have been categorized in one of the four categories enumerated above. In this regard, the prioritization component 424 may utilize one or more third-party risk models to prioritize patients based on a determined level of risk. The prioritization component 424 may also use other parameters to prioritize patients. For instance, demographic factors such as age, geographic location, gender, and the like may be used to prioritize patients. Other factors such as amount of health system utilization, disease burden, and/or healthcare spend may be used to prioritize patients. Scores that measure how impactable a particular patient is to care management may also be used to prioritize the patients. Any and all such aspects, and any variation thereof, are contemplated as being within the scope herein.

The notification component 426 is configured to notify patients, care teams, and/or care managers that a particular patient has been identified as being eligible for care management services. The notification component 426 may also provide a category associated with the patient, and a priority level associated with the patient. Details associated with the notification component 426 will be explained in greater depth below with respect to, for example, the care management outreach service 416.

Figure 5:
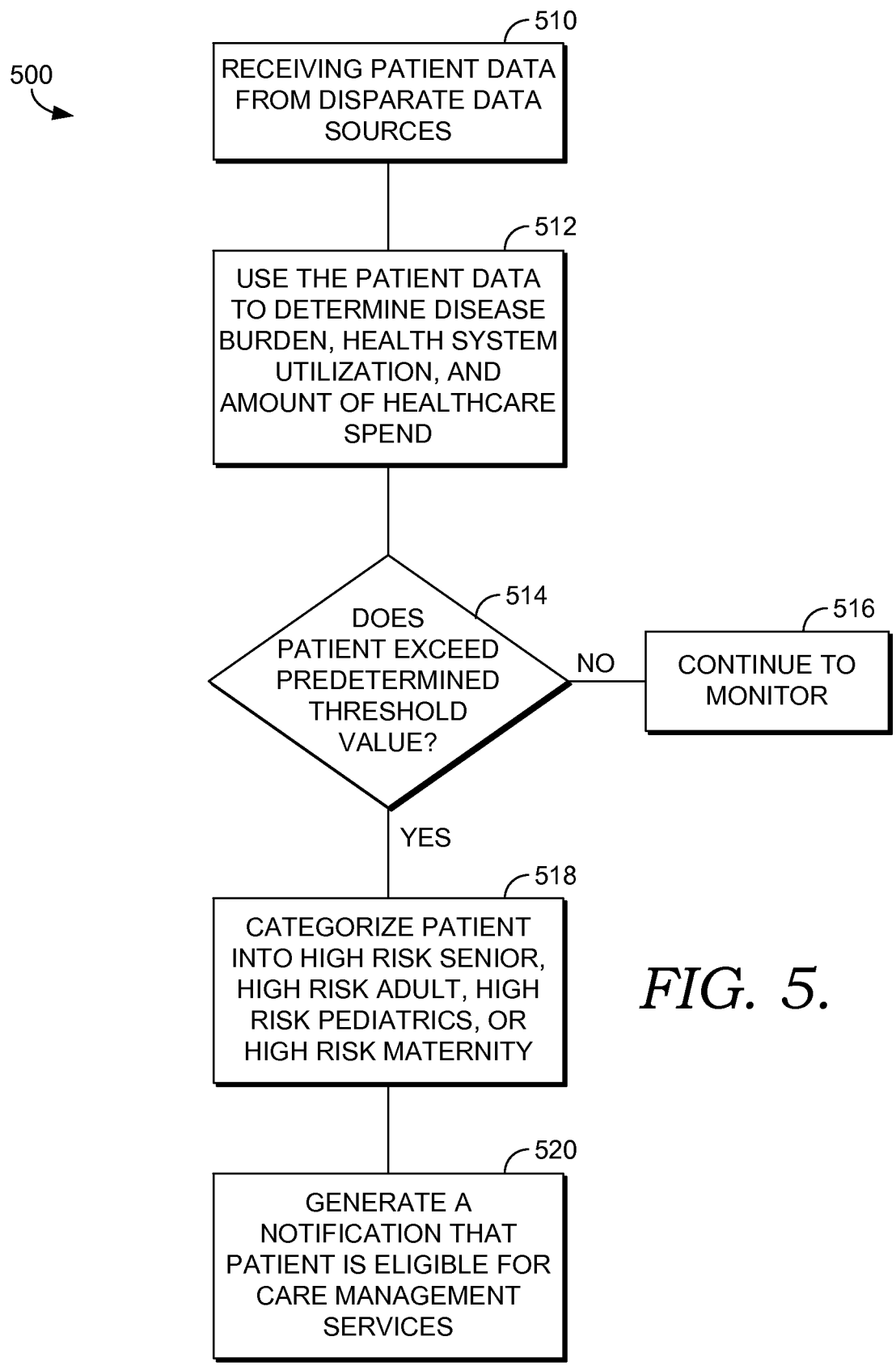
FIGS. 5-7 are flow diagrams illustrating exemplary methods of identifying and stratifying patients within a patient population who are eligible for care management services in accordance with embodiments of the present invention.

Turning now to FIG. 5, a flow diagram is illustrated of an exemplary method 500 of identifying and stratifying a population of patients eligible for care management services. The method 500 may be executed by an identification, stratification, and prioritization service such as the identification, stratification, and prioritization service 412 of FIG. 4. At a step 510, patient health data is received by a receiving component such as the receiving component 418 of FIG. 4 from multiple disparate sources. The patient health data may comprise electronic medical record data received from different healthcare facilities as well as insurance claims data. The sources are disparate in that the sources do not typically share patient data directly with each other. Prior to processing, the patient health data may be compiled into longitudinal patient records for each patient in the population by a longitudinal patient record service such as the longitudinal patient record service 226 of FIG. 2.

At a step 512, for each patient in the population, the patient health data, including the longitudinal patient records, is used to determine a disease burden for each patient, an amount of health system utilization by each patient, and/or an amount of money spent on healthcare services for each patient. This process may be carried out by an identification component such as the identification component 420 of FIG. 4. As previously explained, the identification component may be configured to determine one or more of the criteria for each of the patients. Further, the number of criteria executed against the patient population may be configurable by a client or end-user.

At a step 514, a determination is made by the identification component as to whether a particular patient exceeds a predefined threshold value for one or more of the criteria. Again, the threshold value may be configurable by a client and may be different for each of the selected criteria. If, at a step 516, it is determined that the patient does not exceed the threshold value for one or more of the selected criteria, the patient's health data continues to be monitored. If, however, it is determined at a step 518 that the patient does exceed the threshold value for one or more of the selected criteria, the patient is identified as being eligible for care management services and is categorized into one or more categories by a stratification component such as the stratification component 422 of FIG. 4. Exemplary categories may comprise high-risk senior, high-risk adult, high-risk pediatrics, and high-risk maternity. Subsequent to categorizing the patient, the patient may be prioritized by a prioritization component such as the prioritization component 424 of FIG. 4. Prioritization may be based on a risk model, demographic factors, disease burden, amount of health system utilization, amount of healthcare spend, and the like.

At a step 520, a notification that the patient is eligible for care management services may be generated by a notification component such as the notification component 424 of FIG. 4. The notification may subsequently be communicated to the patient, a care team caring for the patient, a care manager, the patient's guardian or family member, and the like.

Figure 6:
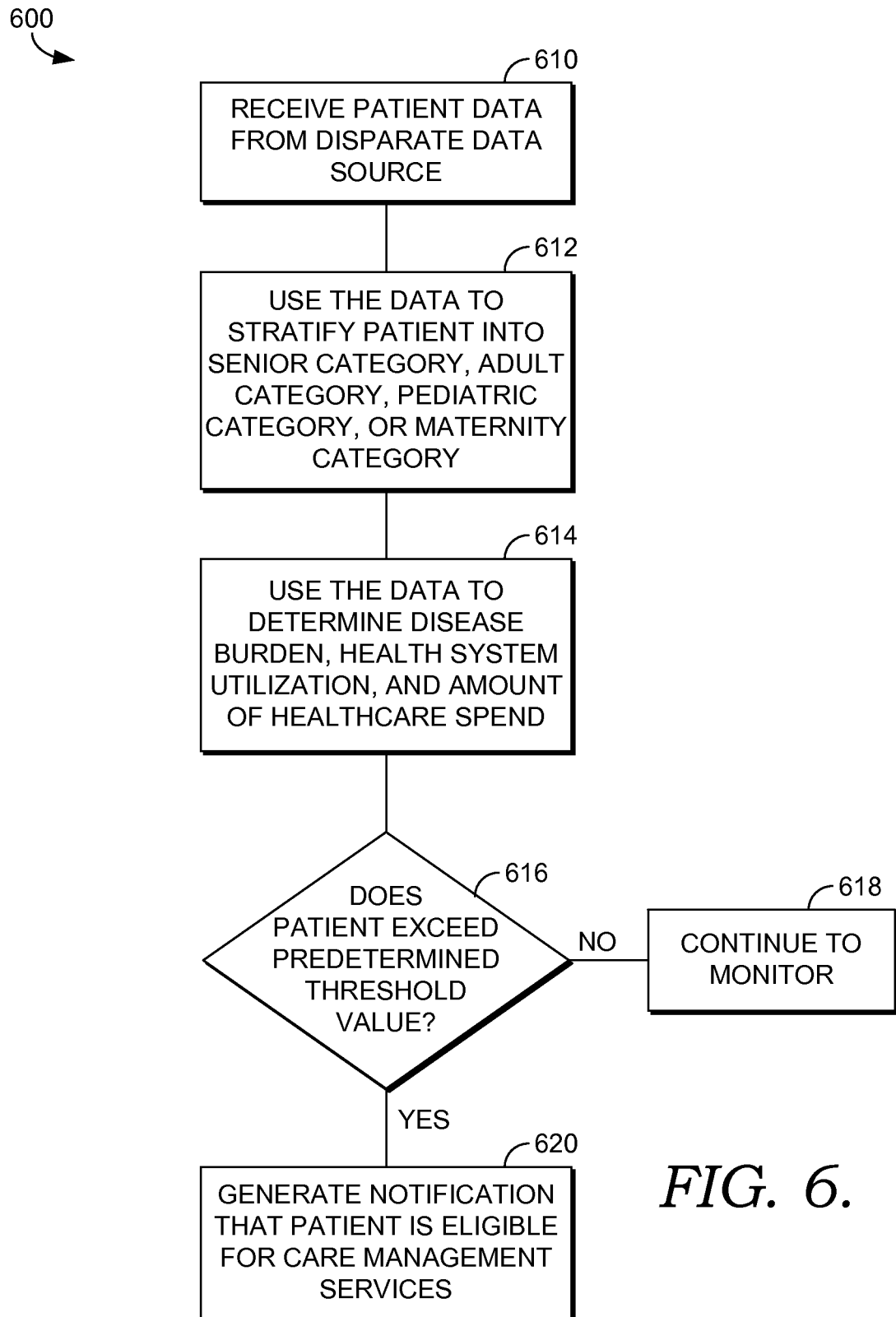

FIG. 6 depicts a flow diagram of an exemplary method 600 of identifying and stratifying a population of patients who are eligible for care management services. At a step 610, patient data for a population of patients is received by a receiving component such as the receiving component 418 of FIG. 4. The data may be communicated by a plurality of disparate data sources. As explained above, the receiving component may be associated with a care management service, such as the care management service 410 of FIG. 4. The care management service may be implemented as part of a cloud computing platform having, for example, processors located at one or more data services center. In turn, a particular data service center may be located at a geographic location that is remote from the geographic locations of the data sources.

At a step 612, the patient data is used to stratify the patients into one of four categories: 1) senior; 2) adult; 3) pediatric; or 4) maternity. This process may be carried out by a stratification component such as the stratification component 422 of FIG. 4. In some instances demographic data, such as age, associated with the population of patients may be used to stratify the patients into one of the four groups. Clinical data may also be used to categorize the patients. In aspects, a particular patient may be categorized into more than one category. For instance, an adult woman may be stratified into both the adult category based on her age and the maternity category if the patient's clinical data indicates she is pregnant.

At a step 614, an identification component, such as the identification component 420 of FIG. 4, identifies a disease burden, an amount of health system utilization, and/or an amount of money spent on healthcare services for each categorized patient. And at a step 616, a determination is made by the identification component 420 whether a particular patient exceeds a respective threshold for one or more of the disease burden, the amount of health system utilization, and/or the amount of healthcare spend. If a particular patient exceeds a respective threshold for one or more of the identification criteria, then, at a step 620, a notification is generated indicating that the patient is eligible for care management services. This may be carried out by a notification component such as the notification component 426 of FIG. 4. The notification may subsequently be communicated to the identified patient, one or more care managers or a care manager supervisor, a care team caring for the patient, and the like. If, however, is it determined that a particular patient does not exceed a threshold value for any of the identification criteria, then, at a step 618, the patient's data continues to be monitored to determine if he/she subsequently becomes eligible for care management services. In aspects, prior to generating a notification, the method 600 may further comprise prioritizing the patients based on, for instance, risk, demographics, disease burden, health system utilization, healthcare spend, and the like.

When comparing FIGS. 5 and 6, it can be seen that in one aspect stratification of patients into different categories may occur prior to identifying whether the patients are eligible for care management services. In an alternative aspect, identification of whether a patient is eligible for care management services may occur first, and stratification of the identified patients may occur after the identification step. In yet another alternative aspect, identification and stratification of patients may be carried out simultaneously. The order in which the identification and stratification operations are executed may be configurable by the end-user, which may comprise a hospital, a healthcare clinic, an insurance company, and the like.

Figure 7:
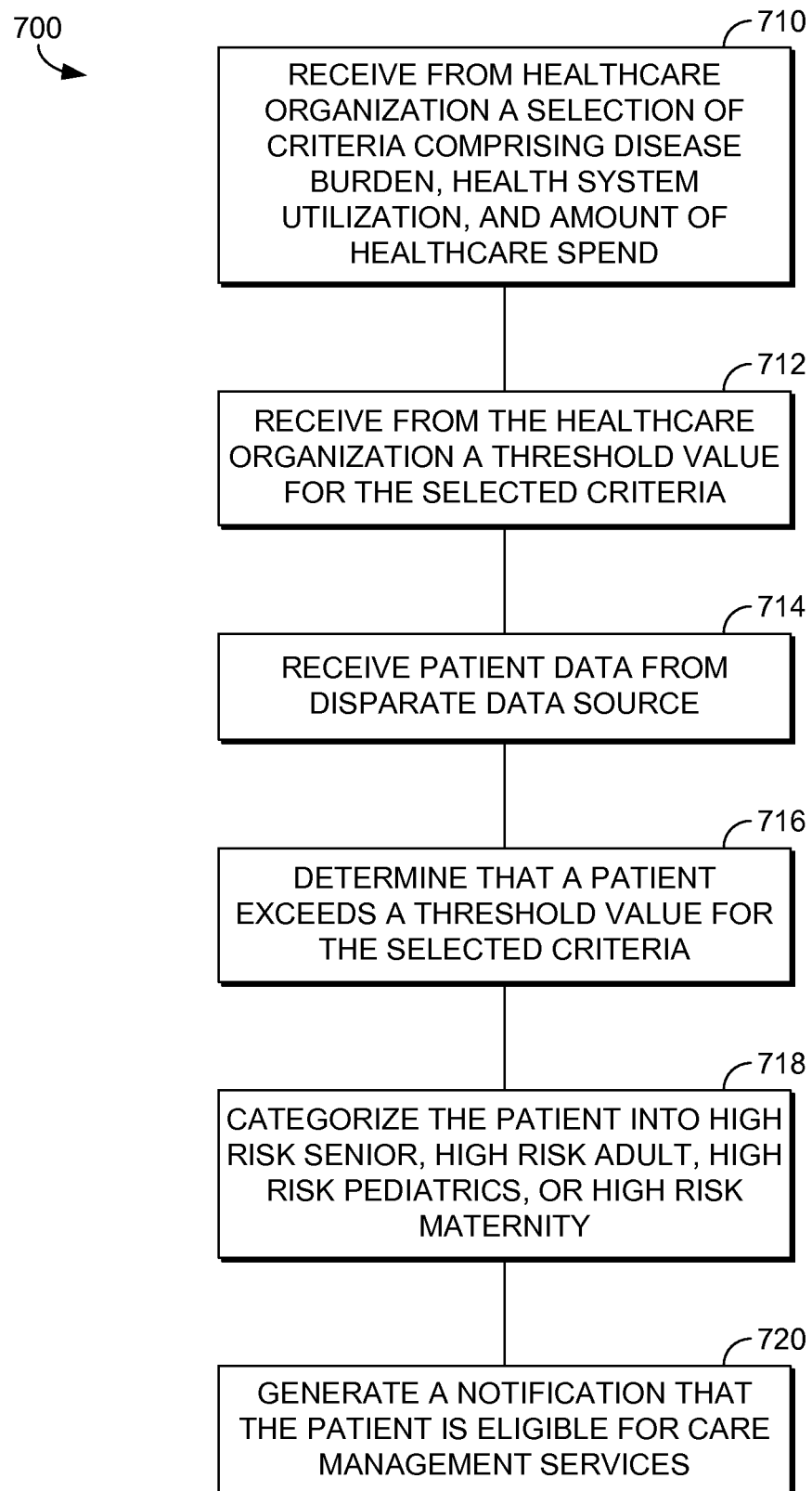

FIG. 7 depicts a flow diagram of an exemplary method 700 of enabling a healthcare organization to identify and stratify patients within a patient population cared for by the healthcare organization who are eligible for care management services. At a step 710, a selection is received from the healthcare organization by a receiving component such as the receiving component 418 of FIG. 4. The selection comprises a selection of one or more criteria used to identify patients who are eligible for care management services. The healthcare organization may select as its criteria a disease burden associated with each patient, an amount of health system utilization by each patient, and/or an amount of money paid for healthcare services for each patient. The healthcare organization may select any one of the criteria, any two of the criteria, or all three of the criteria.

At a step 712, the receiving component receives from the healthcare organization a threshold value for each of the criteria that has been selected by the healthcare organization. For instance, the threshold value may specify a minimum number and/or type of disease conditions, a minimum number of visits to a healthcare facility by the patient within a predefined period of time such as one year, and/or a minimum amount of money spent on healthcare services for the patient.

At a step 714, the receiving component receives patient health data from one or more disparate data sources for each patient within the population cared for by the healthcare organization. At a step 716, an identification component, such as the identification component 420 of FIG. 4, determines that at least one patient within the patient population exceeds the respective threshold value for the selected criteria, and, at a step 718, the identified patient is categorized into one or more of the following categories: 1) high-risk senior; 2) high-risk adult; 3) high-risk pediatric; and/or 4) high-risk maternity. In aspects, the steps 716 and 718 are interchangeable. For example, the end-user may also specify the order of the identification and stratification steps. At a step 720, a notification is generated notifying at least the patient that the patient is eligible for care management services.

The system and methods described above allow clients or end-users, such as healthcare organizations to customize the process for identifying patients in their patient population who are eligible for care management services. End-users are able to customize what criteria are used to identify patients eligible for care management services, as well as to customize the order of identification versus stratification. Further, because the described system and methods utilize up-to-date patient data, patients eligible for care management services can be quickly identified and care management may be implemented at a time when it is most needed. Moreover, because patient data is continually received, the system and methods described allow for a pro-active surveillance approach to care management where patient data is continually monitored to determine if a particular patient, who was previously ineligible for care management services, becomes eligible for the services.

Care Manager Assignment and Alignment

The care manager alignment service 414 is configured to process data associated with a population of patients who have been identified as being eligible for care management services by, for example, the identification, stratification, and prioritization service 412, and align them with care managers best-suited to help the patients meet care management goals. The goals of care management, as outlined above, include improving a patient's health status, coordinating the patient's care across different care venues, reducing the patient's need for medical services, and ultimately decreasing the amount of money spent on healthcare services for the patient. The patient and his/her care manager work together to help achieve these goals. For instance, the patient may have goals related to losing weight or achieving better control of a disease condition. The care manager in this case would work with the patient to help the patient achieve these goals and would also implement processes or services that help meet other goals associated with care management. As an example, the care manager may be responsible for implementing home-based health services in an effort to reduce the number of visits by the patient to the emergency department. In order to foster a good working relationship between the patient and his/her care manager, proper alignment between the patient and a particular care manager is needed.

More particularly, the care manager alignment service 414 processes patient health data for those patients who have been determined to be eligible for care management services in order to determine a patient profile for each patient. The profile includes information such as the physician or healthcare facility currently caring for the patient, a category to which the patient belongs (i.e., high-risk senior, high-risk adult, high-risk pediatrics, or high-risk maternity), a priority level associated with the patient, a geographic location of the patient, clinical characteristics of the patient, patient preferences regarding for example, spoken language, gender of healthcare providers, and the like, the socioeconomic status of the patient, the patient's support system, the patient's ambulation status, the patient's literacy status, the level of contact with the care manager needed by the patient, and the like.

The care manager alignment service 414 further accesses criteria associated with one or more care managers. These criteria may comprise the clinical expertise of the care manager, years of experience of the care manager, a physician or healthcare facility with whom the care manager is affiliated, a geographical location of the care manager, previous care management outcomes associated with the care manager, a workload capacity of the care manager, and the like. Using the patient profile and the criteria associated with the care managers, the care manager alignment service 414 aligns the patient with an appropriate care manager.

As shown in FIG. 4, the care manager alignment service 414 comprises a receiving/accessing component 428, a determining component 430, an alignment component 432, and a notification component 434. In some embodiments, one or more of the components 428, 430, 432, and 434 may be implemented as stand-alone applications. In other embodiments, one or more of the components 428, 430, 432, and 434 may be integrated directly into the operating system of a computing device such as the remote computer 108 of FIG. 1. It will be understood that the components 428, 430, 432, and 434 illustrated in FIG. 4 are exemplary in nature and in number and should not be construed as limiting. Any number of components may be employed to achieve the desired functionality within the scope of embodiments hereof.

The receiving/accessing component 428 is configured to receive patient health data. The patient health data may comprise, for example, insurance claims data, longitudinal patient records compiled by the longitudinal patient record service 325 of FIG. 3, and other types of patient data. The patient data may be received from a variety of disparate data sources and be stored in association with, for instance, the data store 446.

The receiving/accessing component 428 may also be configured to receive data from the identification, stratification, and prioritization service 412. This data may comprise a listing of patients determined to be eligible for care management services, categories to which these patients have been assigned, and/or priority levels associated with the patients. Additionally, the receiving/accessing component 428 is configured to receive selections from one or more end-users. Selections may include requests for an alignment of a particular patient with a care manager, a request to re-align a patient with a different care manager, and the like.

The receiving/accessing component 428 is further configured to access criteria associated with one or more care managers. The criteria may be stored in association with the data store 446. Exemplary criteria may include the clinical expertise of a particular care manager. Expertise areas include general, geriatrics, maternity, adolescents, pediatrics, nutrition, psychiatric, as well as specific disease conditions such as diabetes, hypertension, stroke, and the like. Another criteria is the geographic location of the care manager and whether the care manager is able to travel to see patients. Practice alignment of the care manager is yet another criteria. For instance, the care manager may be aligned with (or employed by) a particular physician, healthcare facility, or insurance provider. Quality and cost outcome data for a particular care manager may also be used as a criteria. Quality and cost outcome data provide an indication of how well patients have done who have been aligned with a particular care manager. This may be measured as an improvement in the patient's health status, a reduction in health system utilization, and/or a reduction in the amount of money spent on healthcare services for the patient.

An additional criteria is the current workload capacity associated with a care manager. Workload capacity is a measure of the current work load of the care manager and takes into account not only the number of patients currently assigned to the care manager but also the need level of the assigned patients. In turn, a patient's need level, which may be quantified by a numerical value between 1 and 100, reflects the amount of contact between the patient and the care manager and the number of care manager tasks associated with the patient. As an example, two patients may have the same two disease conditions but yet the need level of one of the patients is greater than the other. This may be due to an increased severity of the disease conditions, a lack of a social support system, the educational level of the patient, the mental state of the patient, an ambulation status of the patient, and the like. Thus, a particular care manager's workload capacity may be the collective need levels of all the patient's currently assigned to the care manager.

The determining component 430 of the care manager alignment service 414 is configured to use the patient health data to determine a patient profile for each of the patients identified as being eligible for care management services. The patient profile may comprise information such as the physician or healthcare facility currently providing care services to the patient, the geographic location of the patient, a category to which the patient was assigned, a priority level of the patient, clinical characteristics of the patient such as disease conditions, socioeconomic status of the patient, the patient's support system, a behavioral health history, the patient's ambulation status, the patient's literacy status, the patient's nutrition status, and patient preferences regarding such things as preferred spoken language, gender preference for care providers, and the like. After creation, the patient profile may be stored in association with the data store 446 and updated as new patient health data is received by the receiving/accessing component 428.

The alignment component 432 is configured to use the criteria associated with the care managers and the patient profiles to align patients with one or more potential care managers. Alignment may be based on, for example, a degree of similarity between the care manager criteria and the patient profiles. In aspects, a threshold level of similarity is needed before aligning a patient with a particular care manager. This threshold value may be predefined or set by the end-user. When determining the degree of similarity between the criteria and the profiles, some attributes of the patient profiles may be weighted more heavily than others. For instance, factors such as the geographic location of the patient, category assignment of the patient, priority level of the patient, disease conditions of the patient, patient need level, and patient alignment with a particular physician and/or healthcare facility may be weighted more heavily compared to factors such as patient socioeconomic status, literacy status, patient preferences, nutrition status, ambulation status, patient support system, and the like. Likewise, care manager criteria such as clinical expertise, geographical location, workload capacity, and care manager alignment with a particular physician, insurance company, and/or healthcare facility may be weighted more heavily as compared to quality and cost outcome data.

In aspects, the alignment component 432 may be configured to execute a two-pass alignment protocol. The first pass may utilize those patient factors and care manager criteria that are weighted more heavily. The outcome of the first pass may be a pool of care managers (i.e., two to three) for each patient. The alignment component 432 may then execute a second pass that utilizes the less heavily-weighted patient factors and care manager criteria. The outcome of this second pass narrows the pool of care managers to one or possibly two care managers. Any further alignment decision may be made by, for instance, a care manager supervisor.

The notification component 434 is configured to generate notifications notifying the patient and/or the care manager of the assignment. Additional notifications may be generated notifying the patient's physician and/or the patient's family of the care manager assignment. The notification component 434 is additionally configured to communicate the notifications to the patient, care manager, physician, and/or family member via, for example, an email, an automated call, a posting to the patient's Web-based portal, and the like.

Figure 8:
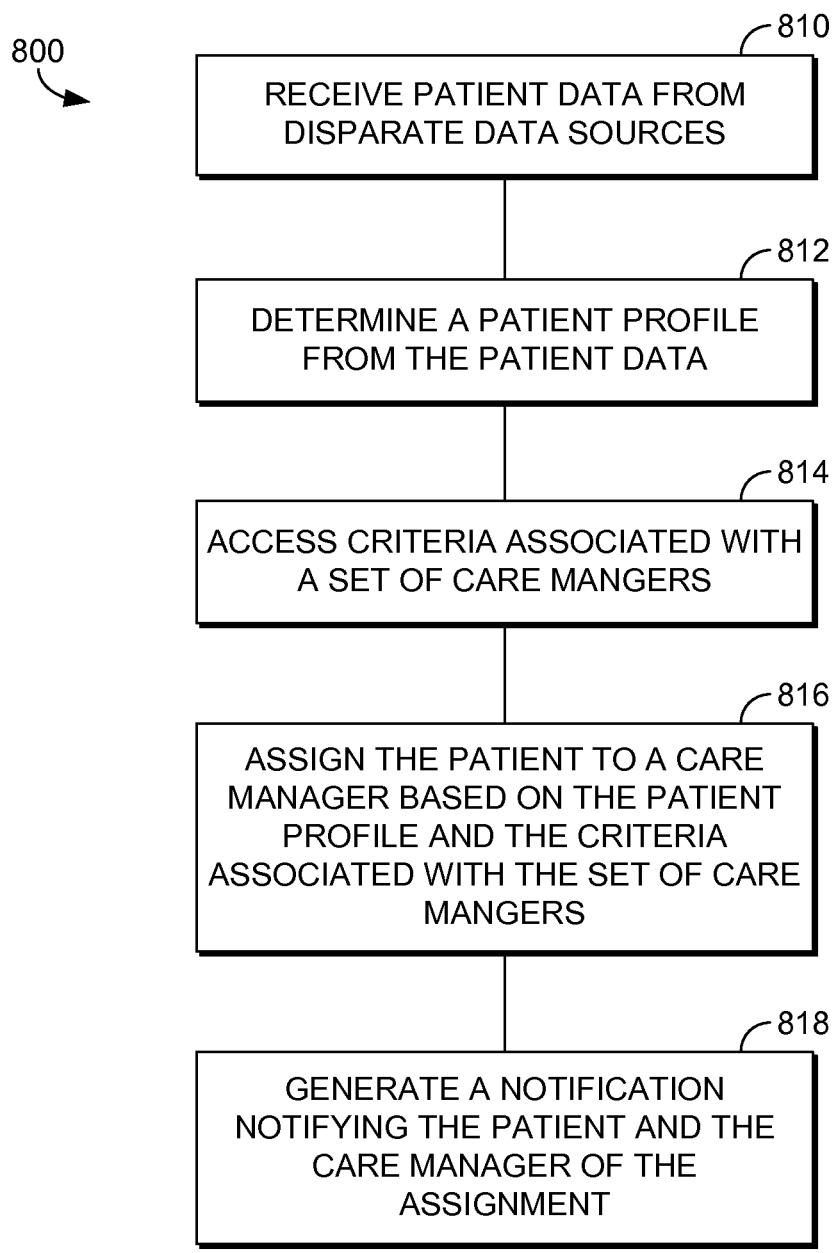
FIGS. 8-10 are flow diagrams illustrating exemplary methods of aligning a patient with a care manager in accordance with embodiments of the present invention.

Turning now to FIG. 8, a flow diagram is depicted of an exemplary method 800 of aligning a patient who is eligible for care management services with an appropriate care manager. At a step 801, patient health data is received from a plurality of disparate sources. The patient health data may be received by a receiving component such as the receiving/accessing component 428 of FIG. 4. The patient health data includes at least insurance claims data and patient longitudinal medical records as well as any outcome data generated by, for instance, an identification, stratification, and prioritization service such as the service 412 of FIG. 4. The disparate data sources may comprise, for instance, any number of healthcare facilities that have provided healthcare services to the patient. Each of these sources may maintain their own electronic medical record system. Further, the disparate data sources typically do not share patient electronic medical record data with each other.

At a step 812, the patient health data is used by a determining component such as the determining component 430 of FIG. 4, to determine a patient profile for each patient who has been identified as being eligible for care management services. The list of patients identified as being eligible for care management services as well as category information and priority level information may be supplied by, for example, the identification, stratification, and prioritization service 412. The patient profile may include information such as a physician or healthcare facility currently providing care to the patient, a category to which the patient is assigned (e.g., high-risk senior, high-risk adult, high-risk pediatric, or high-risk maternity), a priority level of the patient, a geographic location of the patient, clinical characteristics of the patient (i.e., disease conditions associated with the patient), a patient need level, a patient socioeconomic status, a support system associated with the patient, and patient preferences regarding language, preferred gender of care provider, location of healthcare services, and the like.

At a step 814, criteria associated with a set of care managers is accessed by an accessing component such as the receiving/accessing component 428 of FIG. 4. The criteria may comprise a clinical expertise of the care manager, a physician, healthcare facility, or insurance company with whom the care manager is affiliated, a geographical location of the care manager, a current workload capacity of the care manager, and previous care management outcome and cost data associated with the care manager. The clinical expertise, as explained above, may comprise such things as geriatric, pediatric, maternity, a specific disease condition, nutrition, adolescent, and the like. The current workload capacity provides an indication of how many patients are currently assigned to the care manager as well as the cumulative need level of these patients.

At a step 816, an alignment component, such as the alignment component 432 of FIG. 4, uses the patient profile data and the criteria associated with the care managers to assign the patient to a particular care manager. In aspects, the assignment may be based on the similarity between the patient profile data and the care manager criteria. If the degree of similarity is above a predetermined threshold, an assignment may be made.

At a step 818, a notification is generated notifying the patient and/or the care manager of the assignment. This may be carried out by a notification component such as the notification component 434 of FIG. 4. After generation, the notification may be communicated to the patient and/or the patient's care manager.

Figure 9:
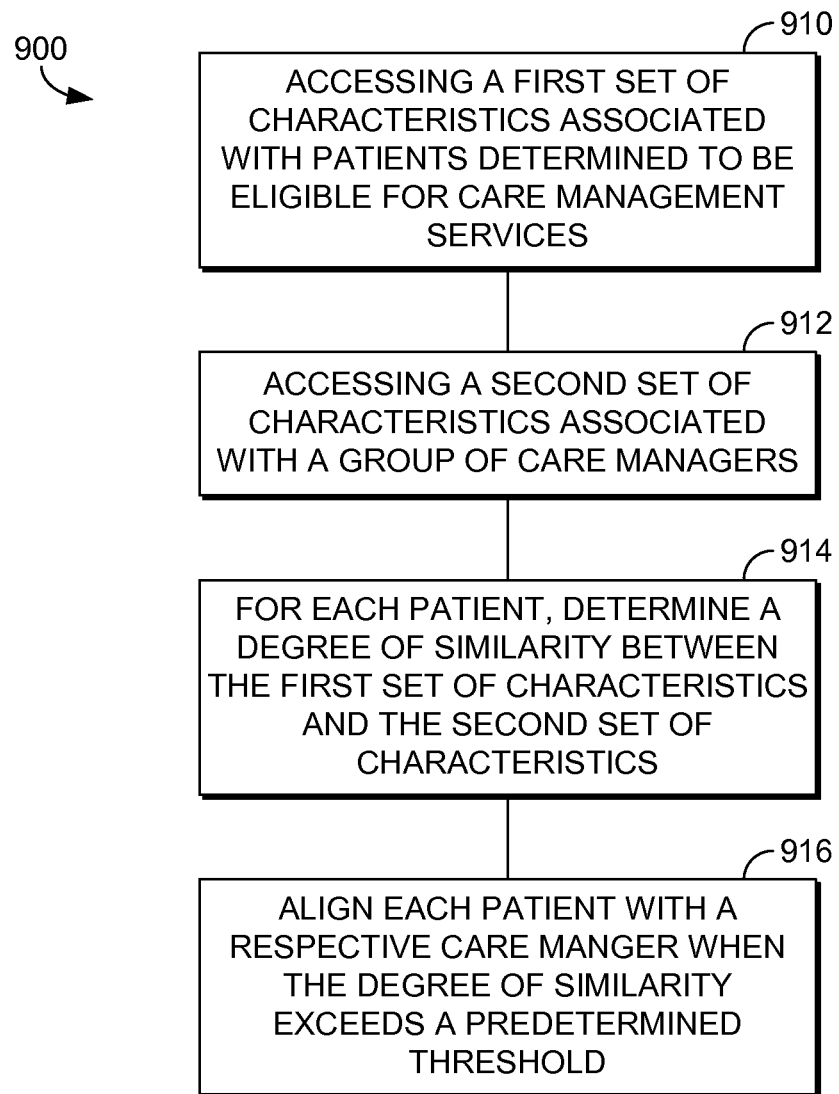

FIG. 9 depicts a flow diagram of an exemplary method 900 of aligning a patient who is eligible for care management services with an appropriate care manager. At a step 910, a receiving/accessing component such as the receiving/accessing component 428 of FIG. 4, accesses a first set of characteristics associated with patients determined to be eligible for care management services. The first set of characteristics may be stored in association with a data store such as the data store 446 of FIG. 4. In aspects, the first set of characteristics may comprise a patient profile for each patient and may include information such as a physician or healthcare facility currently providing care to the patient, a category to which the patient is assigned, a priority level associated with the patient, a geographic location of the patient, clinical characteristics of the patient, a patient need level, a patient socioeconomic status, a support system associated with the patient, an ambulation status, a behavioral health profile, and patient preferences regarding language, preferred gender of care provider, location of healthcare services, and the like.

At a step 912, the receiving/accessing component accesses a second set of characteristics associated with a group of care managers. The second set of characteristics may also be stored in association with a data store such as the data store 446 of FIG. 4. The second set of characteristics may comprise a clinical expertise of the care manager, a physician, healthcare facility, or insurance company with whom the care manager is affiliated, a geographical location of the care manager, a current workload capacity of the care manager, and previous care management outcome and cost data associated with the care manager.

At a step 914, an alignment component, such as the alignment component 432 of FIG. 4, determines a degree of similarity between the first set of characteristics and the second set of characteristics. This process is carried out for each care manager in the group of care managers. And at a step 916, the alignment component aligns the patient with a particular care manager when the degree of similarity is above a predetermined threshold. The threshold, in aspects, may be set by the end-user. The method 900 may further comprise generating a notification indicating the assignment of the patient to the particular care manager.

Figure 10:
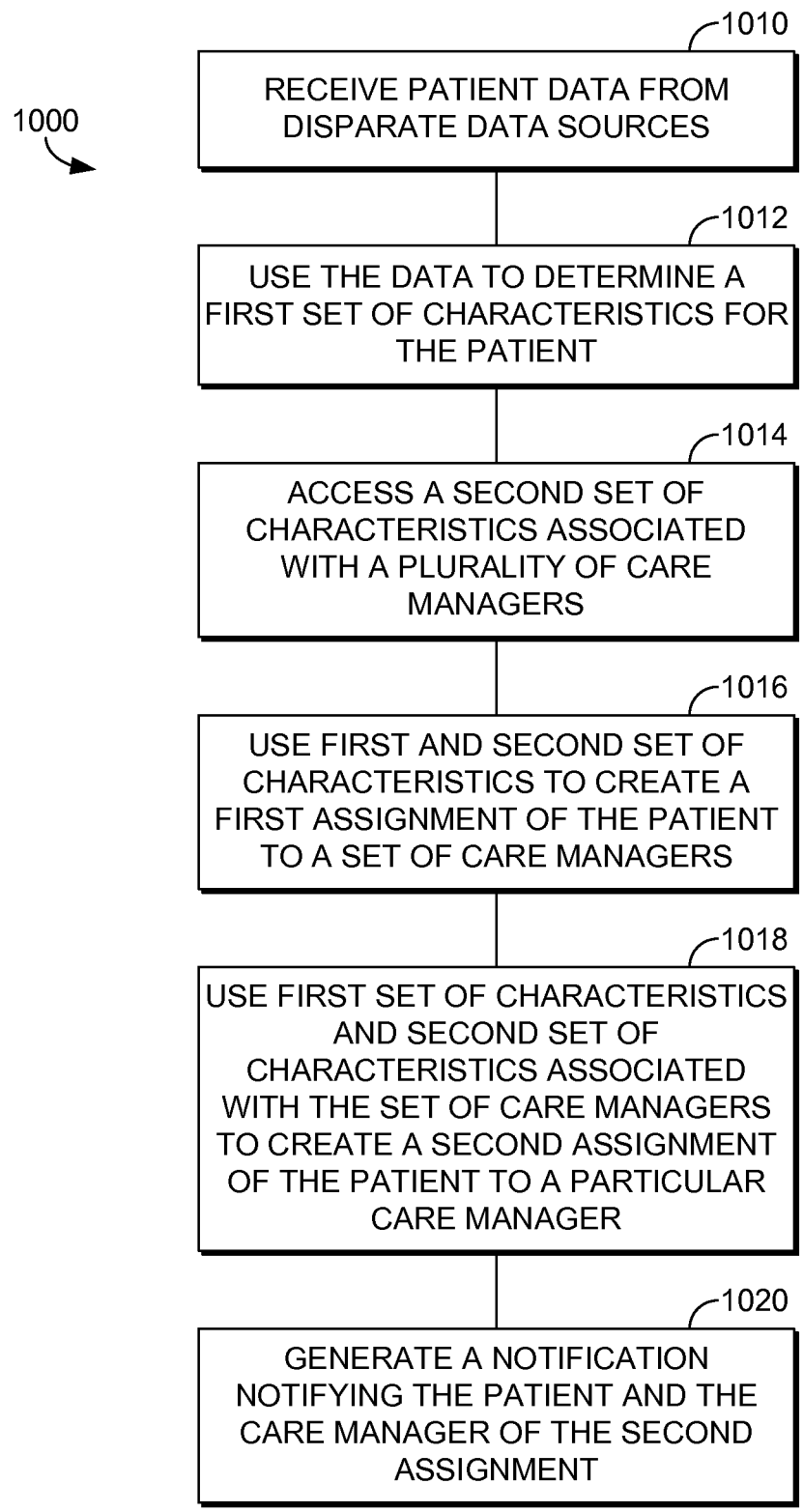

FIG. 10 depicts a flow diagram of an exemplary method 1000 of aligning a patient who is eligible for care management services with a care manager. At a step 1010, patient health data comprising at least patient electronic medical record data and insurance claims data is received from a plurality of disparate data sources by a receiving component such as the receiving/accessing component 428 of FIG. 4.

At a step 1012, a first set of characteristics is determined for the patient using the data where the first set of characteristics may comprise a physician or healthcare facility currently caring for the patient, a category to which the patient is assigned, a priority level associated with the patient, a geographic location of the patient, clinical characteristics of the patient, a patient need level, a patient socioeconomic status, a support system associated with the patient, an ambulation status, a behavioral health profile, and patient preferences regarding language, preferred gender of care provider, location of healthcare services, and the like. The determination may be carried out by a determining component such as the determining component 430 of FIG. 4. In aspects, the different characteristics may be weighted differently. The weighting scheme, in aspects, may be configured by an end-user. For instance, characteristics such as geographic location, a category to which the patient is assigned, a priority level associated with the patient, clinical characteristics, patient need level, and patient alignment with a particular physician or healthcare facility may be weighted more heavily than characteristics such as socioeconomic status, patient preferences, ambulation status, nutrition status, patient support system, and the like.

At a step 1014, a second set of characteristics associated with a plurality of care managers is accessed by an accessing component such as the receiving/accessing component 428 of FIG. 4. The second set of characteristics may comprise a clinical expertise of the care manager, a physician, healthcare facility, or insurance company with whom the care manager is affiliated, a geographical location of the care manager, a current workload capacity of the care manager, and previous care management outcome and cost data associated with the care manager. Certain characteristics in the second set may be weighted more heavily than others. In aspects, the weighting scheme is configurable by an end-user. For instance, characteristics such as clinical expertise, a physician, healthcare facility, and/or insurance provider with whom the care manager is affiliated with, and workload capacity may be weighted more heavily than geographic location, outcome data, and the like.

At a step 1016, the first and second sets of characteristics are used by an alignment component to create a first assignment of the patient to a set of care managers. The set of care managers may comprise two to three care managers. In aspects, the first assignment may be made based on the degree of similarity between the more heavily-weighted characteristics. At a step 1018, the first set of characteristics and the second set of characteristics associated with the set of care managers resulting from the first assignment are used to create a second assignment of the patient to a particular care manager within the set of care managers. In aspects, the second assignment may be made based on a degree of similarity between the less-heavily weighted characteristics. At a step 1020, a notification is generated notifying the patient and the particular care manager of the assignment.

The systems and methods described above leverage longitudinal patient records, care manager criteria, and outcome data from an identification, stratification, and prioritization service to appropriately align patients eligible for care management services with care managers. Proper alignment between patients and care managers helps to facilitate the execution of care management goals.

Care Management Outreach

The care management outreach service 416 is configured to process and monitor patient health data for patients who have been identified as being eligible for care management services (by, for example, the identification, stratification, and prioritization service 412) to: 1) determine if the patient is eligible for one or more care management outreach events; and 2) automatically and without human intervention generate those outreach events. A care management outreach event may be defined as a communication between at least a care manager, or care management service, and a patient that relates to some aspect of care management. The outreach event may also extend to communications between the care manager and a care team (e.g., a physician, a health care facility, a physician assistant, and the like) caring for the patient, and/or between the care manager and a member of the patient's family. The communications may be in the form of a letter, an email, an automated phone call, information posted to the patient's Web-based portal, a text message, and the like.

The outreach events may be triggered in response to a number of different situations. For example, the outreach event may be triggered in response to detecting a change in the patient's care management status. Exemplary status changes may comprise: eligible to enrolled, eligible to declined, enrolled to cancelled, and enrolled to suspended. Upon detection of any of these status changes, an outreach event is automatically generated notifying the patient, the patient's family member, and/or the patient's care team of the status change and providing any additional information associated with the status change.

Another trigger that initiates an outreach event may comprise detection of an update to the patient's care plan. These updates may include a change to one of the care plan goals, documentation of an interaction with the patient, a determination that the patient is eligible for a health maintenance/intervention program, the addition of a new care task, and the like. Again, in response to detecting the update, an outreach event is automatically generated notifying the patient, the patient's family member, and/or the patient's care team of the update and providing any information associated with the update.

As shown in FIG. 4, the care management outreach service 416 comprises a receiving component 436, a monitoring component 438, a populating component 440, and a notification component 442. In some embodiments, one or more of the components 436, 438, 440, and 442 may be implemented as stand-alone applications. In other embodiments, one or more of the components 436, 438, 440, and 442 may be integrated directly into the operating system of a computing device such as the remote computer 108 of FIG. 1. It will be understood that the components 436, 438, 440, and 442 illustrated in FIG. 4 are exemplary in nature and in number and should not be construed as limiting. Any number of components may be employed to achieve the desired functionality within the scope of embodiments hereof.

The receiving component 436 is configured receive patient health data from a plurality of disparate data sources. The patient health data may comprise, for example, insurance claims data, electronic medical record data, longitudinal patient records compiled by the longitudinal patient record service 325 of FIG. 3, and other types of patient data.

The receiving component 436 is also configured to receive information from, for example, the identification, stratification, and prioritization service 412, and the care manager alignment service 414. Information received from the identification, stratification, and prioritization service 412 may comprise a listing of patients eligible for care management services as well as categories to which the patients have been assigned and a priority level associated with the patients. More particularly, the information may comprise a listing of patients along with their contact information and any communication preferences associated with the patients. For example, a patient may have indicated that he prefers to receive communications via email. Information received from the care manager alignment service 414 may comprise a listing of the patients along with their assigned care manager.

The monitoring component 438 is configured to monitor the information received by the receiving component 436 and determine if a care management outreach event has been triggered for a particular patient. For instance, a care management outreach event may be triggered when a care management status change has occurred. Exemplary status changes may comprise a change from a patient being eligible for care management services (as identified by the identification, stratification, and prioritization service 412) to actually enrolling in care management services. Another status change comprises a change from the patient being eligible for care management services to declining to enroll in care management services.

Yet another status change comprises a change from the patient being enrolled in care management services to care management services being cancelled for the patient. This may occur when, for example, the patient's health data indicates that the patient's health status has improved to the point where care management services are no longer necessary, the patient has declined to participate further in the program, or the patient's insurance no longer covers care management services. An additional status change comprises a change from the patient being enrolled in care management services to the care management services being suspended for the patient. Suspension may be due to changes in insurance eligibility, a request by the patient, a change in the patient's health status, and the like.

Besides monitoring status changes, the monitoring component 438 is configured to monitor the patient health data to determine if a particular patient becomes eligible for one or more health intervention programs. Health intervention programs are large-scale programs often launched by a healthcare facility to manage a particular disease condition in its patient population. Patients are identified as being eligible for a particular program when their health data meets certain criteria. For example, a patient may be eligible for an obesity management program when the patient's body mass index (BMI) is above a threshold parameter for a defined period of time. Each of these programs may have an associated set of recommendations. Exemplary health intervention programs include hypertension management programs, diabetes management programs, and obesity management programs.

The monitoring component 438 is further configured to monitor any care management plans associated with a patient and determine if an update has been made to the plan. As used throughout this disclosure, the term "care management plan" comprises a plan designed to help the patient achieve the goals of care management. On a practical level, the care management plan is created by the patient's care manager and includes, for example, goals set by the patient, alerts related to the patient, a listing of encounters, including upcoming encounters, between the patient and healthcare providers, a listing of the patient's care team, clinical data associated with the patient such as lab values and disease conditions, action items, and/or care recommendations. The monitoring component 438 is configured monitor updates to any of these items whether they be in response to a manual update by the patient's care manager or in response to an automatic update due to a change in the patient's health data.

The populating component 440 is configured to receive information from the monitoring component 438 and use this information to automatically and without human intervention select an appropriate template and populate the template with patient-specific information. For example, upon identifying that a patient is eligible for care management services, the populating component 440 may select an "enrollment" template and populate the template with patient-specific information. The enrollment template notifies the patient of her eligibility for care management services and provides information on the services. The enrollment template may be populated with, for instance, the patient's name and other identifying information, and a potential care manager assigned to the patient.

Incident to the monitoring component 438 detecting a change in status from eligible to enrolled, the populating component 440 may select a "welcome-to-service" template and populate the template with patient-specific information. The welcome-to-service template provides in-depth information on the care management program. The patient-specific information populated into the template may comprise at least the patient's name and other identifying information, a designation of the patient's care manager (as determined by the care manager alignment service 414), any recommendations based on the patient's clinical condition, and the like. If the patient has been determined to be eligible for a health intervention program, the welcome-to-service letter may also include information on the program along with any patient-specific recommendations related to the program.

Upon the monitoring component 438 detecting a change in status from active to terminated, the populating component 440 is configured to select a "termination-of-service" template and populate the template with patient-specific information. The termination-of-service template may include general information notifying the patient that the service has been terminated. The patient-specific information may comprise for example, the patient's name and identifying information, the specific reason the service was terminated, and any recommendations regarding the patient's current health state and future health state.

Upon the monitoring component 438 detecting a change in status from active to suspended, the populating component 440 is configured to select a "suspension-of-case" template and populate the template with patient-specific information. The suspension-of-case template may include general information notifying the patient that care management services have been suspended. The patient-specific information may include the patient's name and other identifying information, the specific reasons concerning why the service was suspended, and any recommendations regarding the patient's current health state and future health state.

As described above, the monitoring component 438 is also configured to monitor when an update has been made to the patient's care management plan. In aspects, upon receiving information from the monitoring component 438 regarding the update, the populating component 440 automatically selects an "update" template and populates the template with patient-specific information regarding the update. In other aspects, the populating component 440 may only select and populate an update template when the update falls within one or more categories. Exemplary categories include updates to the patient's goals, updates concerning disease conditions associated with the patient, updates regarding qualifications for health intervention programs, alert updates, and/or updates regarding upcoming encounters with providers. Updates that fall outside these categories may not initiate the automatic selection and population of an update template. In yet another aspect, the populating component 440 may be triggered by an action from the care manager. As an example, the care manager may be provided with a prompt upon detecting that an update has been made to the patient's care plan. The prompt may ask if the care manager would like to create an update notification. If the care manager indicates that she would like to create an update notification, the populating component 440 selects an update template and populates it with patient-specific information regarding the update. If, however, the care manager indicates that she does not wish to create an update notification, a template is not selected and populated.

In aspects, the populating component 440 may be configured to select clinician-specific templates upon detection of a change in case management status for the patient or upon detection of an update. The clinician-specific templates may be formatted differently than the templates that are communicated to the patient. For instance, the clinician-specific templates may just include information regarding the particular change in status or the particular update without including the more general information included in the patient-specific templates (e.g., information about the benefits of the care management service).

The notification component 442 is configured to communicate populated templates to the patient, and/or members of the patient's family. In aspects, the notification component 442 leverages the patient's communication preferences (or family members' communication preferences), as determined from the patient's health data, to determine how best to communicate populated templates. As an example, a patient may have indicated that his preferred mode of communication is email. The notification component 442 uses this information and communicates the populated template to the patient via email.

The notification component 442 is further configured to communicate populated templates to members of the patient's care team. Again, communication preferences associated with members of the patient's care team may be leveraged when communicating the templates. In aspects, the notification component 442 may be configured to communicate all templates generated for the patient to the patient's care team. In other aspects, the notification component 442 may be configured to communicate only certain templates to the patient's care team such as, for example, templates regarding changes in the patient's care management status, and/or templates concerning updates to the patient's care management goals.

Figure 11:
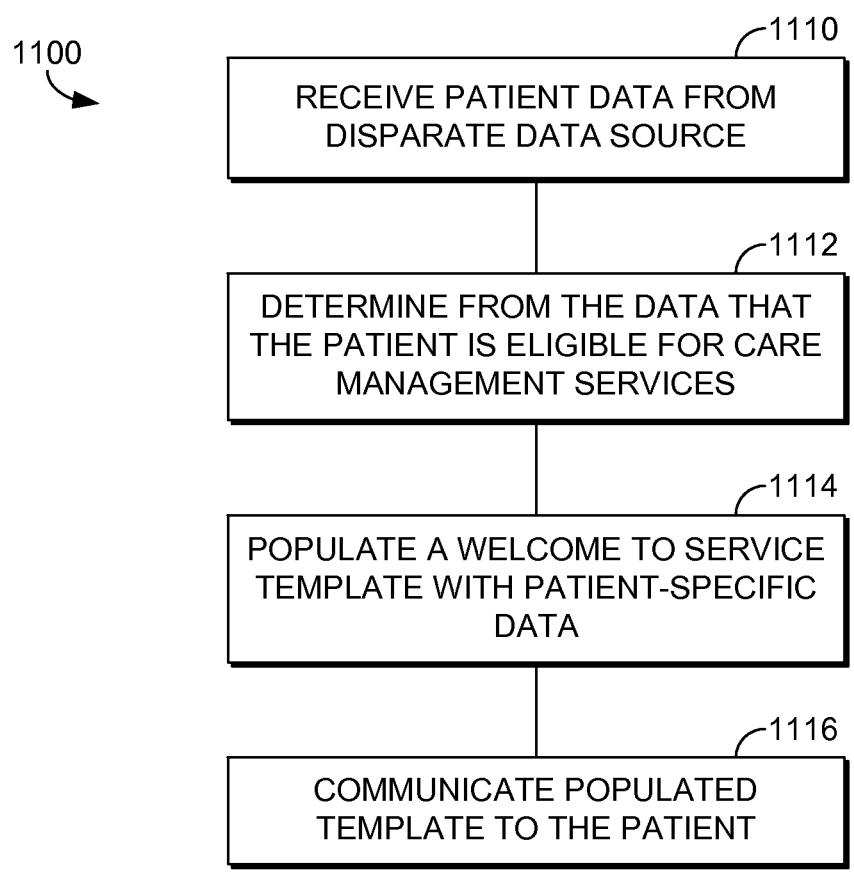
FIGS. 11-13 are flow diagrams illustrating exemplary methods of automatically generating outreach events for a care management service in accordance with embodiments of the present invention.

FIG. 11 depicts a flow diagram of an exemplary method 1100 of generating outreach events for a care management service. The method 1100 may be carried out by a care management service such as the care management service 410 of FIG. 4. At a step 1110 patient data is received by a receiving component (such as the receiving component 436 of FIG. 4) from a plurality of disparate sources.

At a step 1112, it is determined that the patient is eligible for care management services. This process may be carried out by an identification, stratification, and prioritization service such as the service 412 of FIG. 4. In exemplary aspect, the patient is determined to be eligible for care management services when his health data indicates that his disease burden is above a predetermined threshold, the patient's health system utilization is above a predetermined threshold, and/or the amount of money spent on the patient's healthcare services is above a predetermined threshold.

At a step 1114, a welcome-to-service template is automatically selected and populated with patient-specific information by a populating component such as the populating component 440 of FIG. 4. The patient-specific information may be derived from the patient's health data and include the patient's name and other identifying information, a care manager that has been assigned to the patient, any care recommendations specific to the patient, and the like.

At a step 1116, the populated template is communicated to the patient by a notification component such as the notification component 442 of FIG. 4. The template may be communicated to the patient based on preferred-mode-of-communication preferences specified by the patient and as indicated in the patient's health data. The populated template may also be communicated to the patient's care team and/or members of the patient's family.

Figure 12:
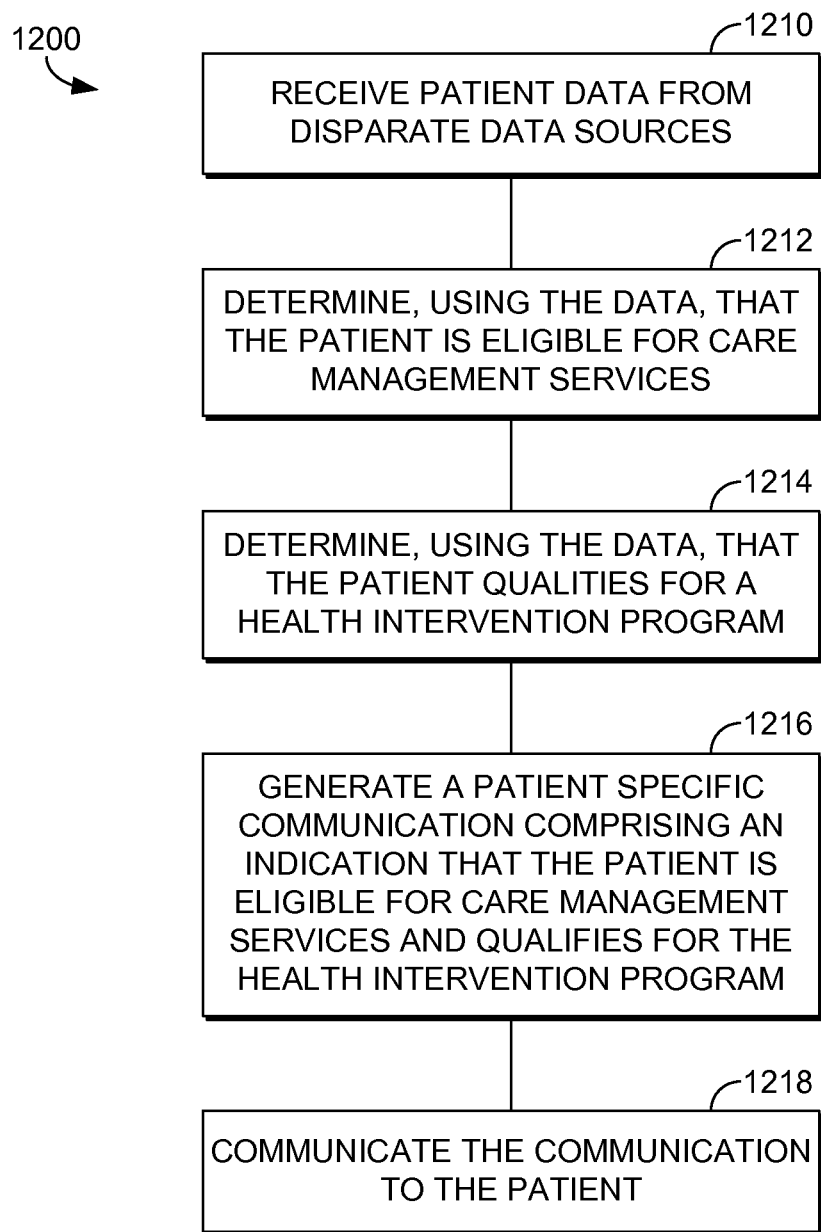

Turning now to FIG. 12, a flow diagram is depicted of an exemplary method 1200 of generating outreach events for a care management service. At a step 1210, a receiving component such as the receiving component 436 of FIG. 4 receives patient health data from a plurality of disparate sources. The patient health data may comprise patient electronic medical record data as well as insurance claims data. At a step 1212, similar to the step 1112 of the method 1100, the patient health data is used to determine that the patient is eligible for care management services.

At a step 1214, it is further determined that the patient qualifies for a health intervention program, where the health intervention program has an associated set of recommendations. This determination may be carried out by a monitoring component such as the monitoring component 438 of FIG. 4. To determine that the patient qualifies for the health intervention program, the patient's health data is analyzed to determine if it meets certain criteria associated with the health intervention program. For example, a patient may qualify for a hypertension management program if the patient's systolic and diastolic pressures are above a threshold value for four consecutive measurements taken over a year period.

At a step 1216, a patient-specific communication is automatically and without human intervention generated. For example, a populating component, such as the populating component 440 of FIG. 4, selects a particular template upon being notified that the patient is eligible for care management services. In exemplary aspects, the template may comprise a welcome-to-service template. The populating component then populates the template with patient-specific information such as the patient's name and other identifying information. The populating component further populates the template with information regarding the patient's qualification for the health intervention program along with any recommendations associated with the program.

At a step 1218, the patient-specific communication is communicated to the patient, and, optionally, the patient's care team and/or family members according to preferred-mode-of-communication preferences indicated by the patient and/or the patient's care team. This may be carried out by a notification component such as the notification component 442 of FIG. 4.

The method 1200 may continue with the monitoring component continually monitoring the patient's health data to determine if a care management status change has occurred such as a change from eligible to enrolled, eligible to declined, enrolled to terminated, or enrolled to suspended. Upon detection of a status change, the populating component selects an appropriate template and populates it with patient-specific information. The template with the status change information may then be communicated to the patient, and, optionally, the patient's care team and/or family members.

The method 1200 may further comprise monitoring, via the monitoring component, any care management plans that have been implemented for the patient to see if an update to the care plan has been made. Updates may be made automatically or upon input by the patient's care manager and may include such things as updates to care management goals, updates regarding care recommendations, updates regarding qualification for health intervention programs, and the like. Upon detection of an update, the populating component may select an update template and populate it with information regarding the particular update. The populated template may then be communicated to the patient, and, optionally, the patient's care team and/or family members by the notification component.

Figure 13:
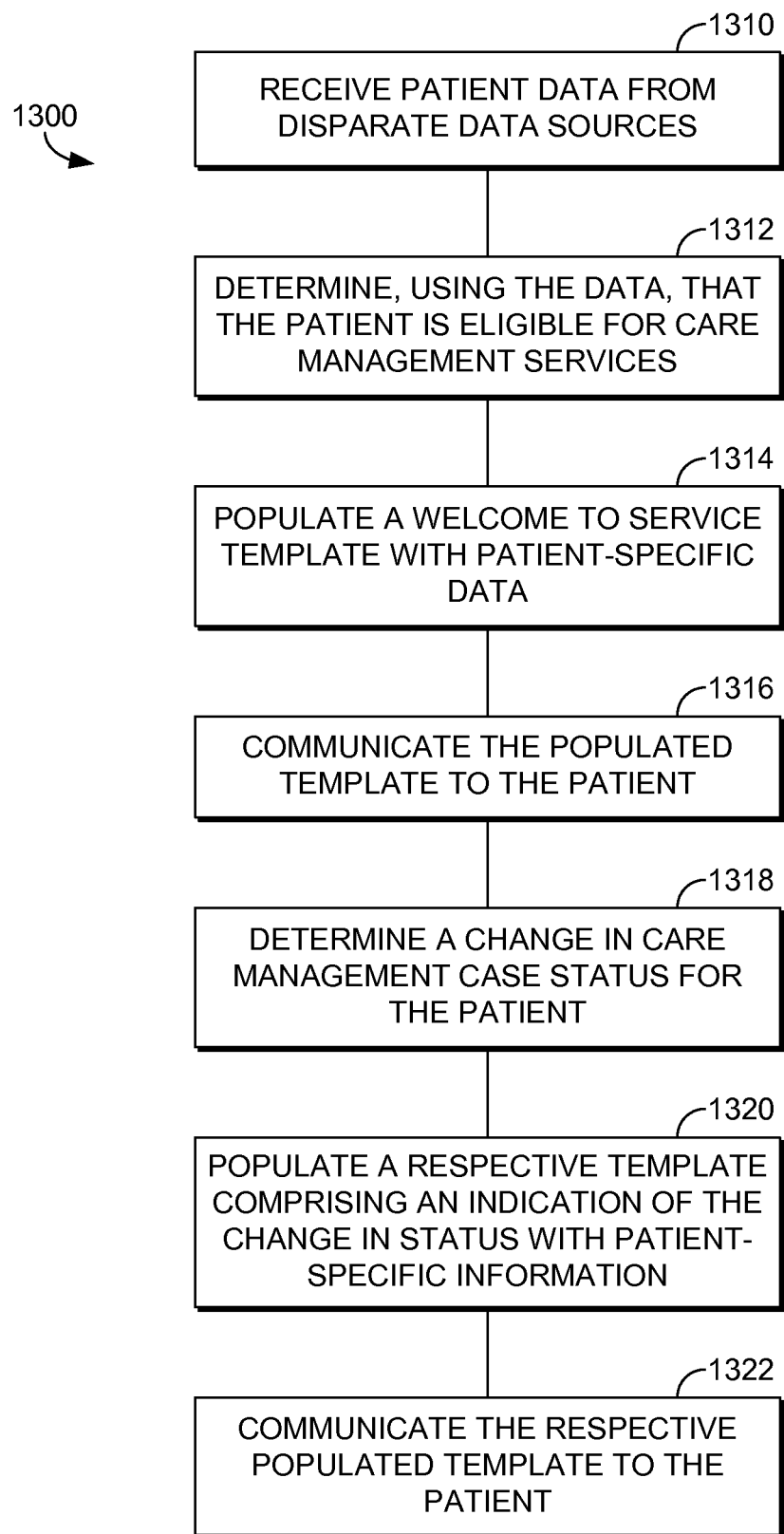

FIG. 13 depicts a flow diagram of an exemplary method 1300 of generating care management outreach events based on a change in a patient's care management status. At a step 1310, patient health data is received by a receiving component, such as the receiving component 436 of FIG. 4, from a plurality of disparate data sources; the patient health data comprises at least patient electronic medical record data and insurance claims data. At a step 1312, the patient health data is used to determine that the patient is eligible for care management services. This may be carried out by an identification component such as the identification component 420 of FIG. 4.

Based on determining that the patient is eligible for care management services, at a step 1314 a welcome-to-service template is automatically selected and populated with patient-specific data. This process may be carried out by a populating component such as the populating component 440 of FIG. 4. And, at a step 1316, the populated welcome-to-service template is communicated to the patient by, for example, a notification component such as the notification component 442 of FIG. 4.

At a step 1318, a monitoring component such as the monitoring component 438 of FIG. 4, determines that there has been a change in care management status for the patient. The change in status may comprise, for example: 1) eligible to declined; 2) eligible to enrolled; 3) enrolled to terminated; or 4) enrolled to suspended. At a step 1320, the populating component selects a template based on the particular change in status and populates the template with patient-specific information regarding the particular update. At a step 1322, the populated template with information regarding the status change is communicated to the patient by a notification component. The template may also be communicated to the patient's care team and/or the patient's family members.

The systems and methods described above utilize the patient health data to timely identify when an outreach event is triggered. In response to detecting the trigger, a care management outreach event is automatically generated and communicated to the patient. Generating these types of outreach events helps to ensure that the patient and the patient's care team are kept apprised of all aspects of care management.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. One or more non-transitory computer-readable media having computer-executable instructions embodied thereon that, when executed by a computing device, perform a method of generating outreach events for a care management service, the method comprising:

continuously receiving, by a server in a cloud computing platform, the server having a processor coupled to a memory and communicating through a computer network with a plurality of remote computing devices of disparate data sources, data associated with a patient, wherein the data include updates to the patient's health data from one or more end-user computing devices, wherein the data is from the plurality of disparate data sources, wherein the data from one or more of the plurality of disparate data sources is in a non-standard format, and wherein disparate data sources are data sources that do not share patient health data with each other;

creating, by the server, a longitudinal medical record comprising electronic medical documentation relevant to the patient's condition and treatment over the lifetime of the patient from the data associated with the patient received from the plurality of disparate data sources, wherein the longitudinal medical record is created by the server by transforming the data from the non-standard format to a standard format and into industry-standard nomenclature using algorithms and techniques including cleaning, standardizing, natural language processing, and machine learning, and wherein the data comprises at least insurance claims data and patient electronic medical record data;

storing, by the server, the longitudinal medical record in one or more data stores associated with the cloud computing platform;

providing, by the server, remote access to the one or more end-user computing devices, wherein the one or more end-user computing devices include the plurality of remote computer devices of the disparate data sources;

determining, by the server, from the longitudinal medical record for the patient that the patient is eligible for the care management services, wherein determining from the longitudinal medical record for the patient that the patient is eligible for the care management services comprises 1) identifying at least disease conditions, an amount of health system utilization, and an amount of healthcare services spent for the patient, 2) stratifying the patient as either senior, adult, pediatrics, or maternity, and 3) prioritizing the patient based on a risk level from items (1) and (2) and how impactful care management services can be on the patient;

based on determining that the patient is eligible for the care management services, automatically and without human intervention populating, by the server, a first template with patient-specific data;

communicating, by the server, the populated first template through the computer network to the one or more end-user computing devices, by generating a graphical user interface which displays the populated template via a display of the one or more end-user computing devices;

identifying in the received data, by the server, an update in at least one of a care management status, a care management plan, and a health data that meets a criteria for one or more health intervention, by continuously monitoring the data being continuously received from the plurality of disparate data sources;

responsive to identifying an update in the data continuously received from the plurality of disparate data sources, automatically and without human intervention customizing and populating, by the server, at least one template corresponding to the identified update with patient-specific information; and communicating, by the server, the at least one populated template through the computer network to the one or more end-user computing devices, by generating a second graphical user interface which displays the at least one populated template via a display of the one or more end-user computing devices.

2. The media of claim 1, wherein determining from the longitudinal medical record that the patient is eligible for the care management services comprises:

using the longitudinal medical record to determine: (1) a disease burden associated with the patient, (2) an amount of health system utilization by the patient, and (3) an amount of money spent on healthcare services for the patient; and determining that the patient exceeds a predetermined threshold value associated with one or more of the disease burden, the amount of health system utilization, or the amount of money spent on healthcare services.

3. The media of claim 1, wherein the disparate data sources comprise a plurality of healthcare facilities that have cared for the patient.

4. The media of claim 3, wherein the plurality of healthcare facilities do not share patient electronic medical record data with each other.

5. The media of claim 4, wherein the data is received at a central processing location.

6. The media of claim 5, wherein the central processing location processes the patient electronic medical record data into the longitudinal medical record for the patient.

7. The media of claim 1, wherein the patient-specific data that is populated into the welcome-to-service template is derived from the patient electronic medical record data.

8. The media of claim 1, wherein communicating the populated template to the patient comprises at least one of presenting the populated template in a patient portal interface used by the patient or sending an email to the patient.

9. The media of claim 1, further comprising communicating an indication that the patient is eligible for the care management services to a physician or healthcare facility currently caring for the patient.

10. A computerized method carried out by at least one server having at least one processor for performing a method of generating outreach events for a care management service, the method comprising:

continuously receiving, by a server in a cloud computing platform, the server having a processor coupled to a memory and communicating through a computer network with a plurality of remote computing devices of disparate data sources, data associated with a patient, wherein the data include updates to the patient's health data from one or more end-user computing devices, wherein the data is from the plurality of disparate data sources, wherein the data from one or more of the plurality of disparate data sources is in a non-standard format, and wherein disparate data sources are data sources that do not share patient health data with each other;

creating, by the server, a longitudinal medical record comprising electronic medical documentation relevant to the patient's condition and treatment over the lifetime of the patient from the data associated with the patient received from the plurality of disparate data sources, wherein the longitudinal medical record is created by the server by transforming the data from the non-standard format to a standard format and into industry-standard nomenclature using algorithms and techniques including cleaning, standardizing, natural language processing, and machine learning, and wherein the data comprises at least insurance claims data and patient electronic medical record data;

storing, by the server, the longitudinal medical record in one or more data stores associated with the cloud computing platform;

providing, by the server, remote access to the one or more end-user computing devices, wherein the one or more end-user computing devices include the plurality of remote computer devices of the disparate data sources;

determining, by the server, from the longitudinal medical record, using the at least one processor, that the patient is eligible for the care management services, wherein determining from the longitudinal medical record that the patient is eligible for the care management services comprises 1) identifying at least disease conditions, an amount of health system utilization, and an amount of healthcare services spend for the patient, 2) stratifying the patient as either senior, adult, pediatrics, or maternity, and 3) prioritizing the patient based on a risk level from items (1) and (2) and how impactful care management services can be on the patient;

further determining, by the server, from the longitudinal medical record, that the patient qualifies for a health intervention program, wherein the health intervention program includes a set of program recommendations;

automatically and without human intervention generating, by the server, a first patient-specific communication comprising an indication that the patient is eligible for the care management services, an indication that the patient qualifies for the health intervention program, and the set of program recommendations;

communicating, by the server, through the computer network, the first communication to the one or more end-user computing devices, by generating a graphical user interface which displays the populated template via a display of the one or more end-user computing device;

identifying in the received data, by the server, an update in at least one of a care management status, a care management plan, and a health data that meets a criteria for one or more health intervention, by continuously monitoring the data being continuously received from the plurality of disparate data sources;

responsive to identifying an update in the data continuously received from the plurality of disparate data sources, automatically and without human intervention customizing and populating, by the server, at least one template corresponding to the identified update with patient-specific information; and communicating, by the server, the at least one populated template through the computer network to the one or more end-user computing devices, by generating a second graphical user interface which displays the at least one populated template via a display of the one or more end-user computing devices.

11. The method of claim 10, further comprising communicating the first communication to a physician or healthcare facility currently caring for the patient.

12. The method of claim 10, further comprising:
receiving an indication that the patient has declined care management services;
automatically and without human intervention generating a second patient-specific communication comprising an indication that the patient has declined care management services; and
communicating the second patient-specific communication to the patient.

13. The method of claim 12, further comprising communicating the second patient-specific communication to a physician or healthcare facility caring for the patient.

14. The method of claim 10, further comprising:
receiving an indication that the patient has enrolled in the care management services;
subsequently determining that the patient is no longer eligible for the care management services;
automatically and without human intervention generating a second patient-specific communication comprising an indication that the patient is no longer eligible for the care management services; and
communicating the second communication to the patient.

15. The method of claim 14, further comprising communicating the second communication to a physician or healthcare facility caring for the patient.

16. The method of claim 10, further comprising:
receiving an indication that the patient has enrolled in the care management services;
receiving an indication that one or more care plan goals for the patient has been documented or has been updated;
automatically and without human intervention generating a second patient-specific communication comprising an indication that the one or more care plan goals has been documented or has been updated; and
communicating the second patient-specific communication to the patient.

17. The method of claim 16, further comprising communicating the second patient-specific communication to a physician or a healthcare facility currently caring the patient.

18. One or more non-transitory computer-readable media having computer-executable instructions embodied thereon that, when executed by a computing device, perform a method of generating outreach events based on a change in patient status, the method comprising:

continuously receiving, by a server in a cloud computing platform, the server having a processor coupled to a memory and communicating through a computer network with a plurality of remote computing devices of disparate data sources, data associated with a patient, wherein the data include updates to the patient's health data from one or more end-user computing devices, wherein the data is from the plurality of disparate data sources, wherein the data from one or more of the plurality of disparate data sources is in a non-standard format, and wherein disparate data sources are data sources that do not share patient health data with each other;

creating, by the server, a longitudinal medical record comprising electronic medical documentation relevant to the patient's condition and treatment over the lifetime of the patient from the data associated with the patient received from the plurality of disparate data sources, wherein the longitudinal medical record is created by the server by transforming the data from the non-standard format to a standard format and into industry-standard nomenclature using algorithms and techniques including cleaning, standardizing, natural language processing, and machine learning, and wherein the data comprises at least insurance claims data and patient electronic medical record data;

storing, by the server, the longitudinal medical record in one or more data stores associated with the cloud computing platform;

providing, by the server, remote access to the one or more end-user computing devices, wherein the one or more end-user computing devices include the plurality of remote computer devices of the disparate data sources;

determining, by the server, from the longitudinal medical record that the patient is eligible for the care management services, wherein determining from the longitudinal medical record that the patient is eligible for the care management services comprises 1) identifying at least disease conditions, an amount of health system utilization, and an amount of healthcare services spend for the patient, 2) stratifying the patient as either senior, adult, pediatrics, or maternity, and 3) prioritizing the patient based on a risk level from items (1) and (2) and how impactful care management services can be on the patient;

based on determining that the patient is eligible for care management services, automatically and without human intervention populating, by the server, a first template with patient-specific data;

communicating, by the server, the populated first template through the computer network to the one or more end-user computing devices by generating a graphical user interface which displays the populated template via a display of the one or more end-user computing devices;

subsequently determining, by the server, a change in care management case status for the patient, the change in care management case status comprising one of: (1) eligible to active, (2) eligible to declined, (3) active to terminated, or (4) active to suspended;

based on the particular change in care management status, automatically and without human intervention customizing and populating, by the server, a respective template corresponding to the identified update with patient-specific data, the respective template comprising an indication of the particular change in status; and communicating, by the server, the respective populated template through the computer network to the one or more end-user computing devices by generating a graphical user interface which displays the populated template via a display of the one or more end-user computing devices.

19. The media of claim 18, further comprising communicating the respective populated template to a physician or a healthcare facility currently caring for the patient.

20. The media of claim 18, further comprising monitoring the data to determine a subsequent change in care management status.

* * * * *